United States Patent [19]

Grundy et al.

[11] Patent Number: 5,855,629
[45] Date of Patent: Jan. 5, 1999

[54] ALKOXY ACETIC ACID DERIVATIVES

[75] Inventors: Michael John Grundy, Thornton, Great Britain; David Roy Kendall, Chester, United Kingdom; Thomas Webster Naisby; Andrew Czeslaw Sutkowski, both of Thornton, Great Britain

[73] Assignee: Shell Oil Company, Houston, Tex.

[21] Appl. No.: 845,713

[22] Filed: Apr. 25, 1997

[30] Foreign Application Priority Data

| Apr. 26, 1996 | [EP] | European Pat. Off. | 96302953 |
| Dec. 6, 1996 | [EP] | European Pat. Off. | 96308886 |

[51] Int. Cl.$^6$ ................ C10L 1/22; C10L 1/18
[52] U.S. Cl. ................ 44/400; 44/389; 44/418; 44/419; 564/170; 564/175; 564/201; 564/203; 560/60; 560/61; 560/187
[58] Field of Search ................ 44/418, 419, 389, 44/400; 564/170, 175; 560/60, 61, 187

[56] References Cited

U.S. PATENT DOCUMENTS

| 3,836,469 | 9/1974 | Miller | 44/400 |
| 3,871,837 | 3/1975 | Bedague et al. | 44/389 |
| 4,125,382 | 11/1978 | O'Brien et al. | 44/389 |
| 4,778,481 | 10/1988 | Courtney | 44/419 |
| 5,024,678 | 6/1991 | Mertens-Gottselig et al. | 44/400 |
| 5,211,721 | 5/1993 | Sung et al. | 44/400 |
| 5,298,038 | 3/1994 | Hashimoto et al. | 44/419 |
| 5,527,364 | 6/1996 | Russo et al. | 44/418 |
| 5,567,211 | 10/1996 | Russo et al. | 44/418 |
| 5,569,310 | 10/1996 | Cherpeck | 44/400 |

FOREIGN PATENT DOCUMENTS 2407258 6/1979 France.

*Primary Examiner*—Ellen M. McAvoy

[57] ABSTRACT

This invention provides alkoxy acetic acid derivatives of general formula I:

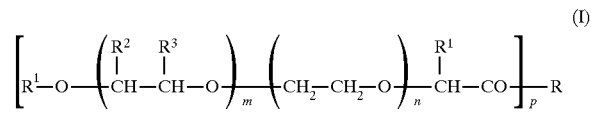

wherein R is the residue of an amine, an aminoalcohol or a polyol linked to the or each —CHR'—CO— moiety via an amide or ester linkage;

R' is hydrogen or a $C_{1-4}$ alkyl group;

$R^1$ is an optionally substituted hydrocarbyl group of 1 to 300 carbon atoms;

one of $R^2$ and $R^3$ is independently selected from hydrogen and optionally substituted hydrocarbyl of 1 to 10 carbon atoms, the other of $R^2$ and $R^3$ being independently selected from optionally substituted hydrocarbyl of 1 to 10 carbon atoms;

m is from 3 to 200;

n is from 0 to 20, provided that m/n is at least 1; and p is from 1 to 5; a process for their preparation; and their incorporation in additive concentrates and fuel compositions for internal combustion engines.

41 Claims, No Drawings

ALKOXY ACETIC ACID DERIVATIVES

FIELD OF THE INVENTION

The present invention relates to alkoxy acetic acid derivatives, processes for their preparation, and their incorporation in additive concentrates and fuel compositions for internal combustion engines.

BACKGROUND OF THE INVENTION

FR-A-2 407 258 (Rhone-Poulenc) discloses fuel compositions comprising a motor fuel and at least one alkylpolyglycol acetic acid amide having the formula:

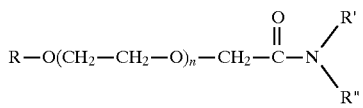

wherein R represents a saturated or unsaturated $C_{8-20}$, preferably $C_{12-18}$, aliphatic radical, R' represents hydrogen or a saturated or unsaturated aliphatic radical of at least 3, preferably 4 to 18, carbon atoms, and R" represents a saturated or unsaturated aliphatic radical of at least 3, preferably 4 to 18, carbon atoms. In the examples, there are described additives of the above formula in the form (1) of the N,N-dibutylamide of the acid derived from a 45:55 mixture of polyethoxylated cetyl and oleyl alcohols ($C_{16}$ saturated and $C_{18}$ unsaturated alcohols) wherein n is 6.3, (2) of the N-dodecylamide of the acid derived from a 75:25 mixture of polyethoxylated dodecyl and tetradecyl alcohols wherein n is 4.5 and (3) of the N,N-dibutylamide of the acid from which (2) is derived. The amides are said to impart improved detergency, anti-corrosion, anti-pollution and anti-icing properties to hydrocarbon fuels.

SUMMARY OF THE INVENTION

There has now been discovered a novel class of alkoxy-acetic acid derivatives which may be incorporated in fuel compositions for internal combustion engines, members of which class have been found to give rise to advantageous engine cleanliness effects.

According to the present invention, there are provided alkoxy acetic acid derivatives of general formula I:

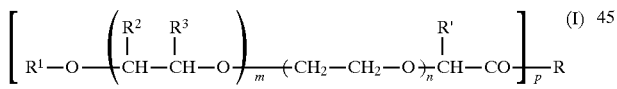

wherein R is the residue of an amine, an aminoalcohol or a polyol linked to the or each —CHR'CO— moiety via an amide or ester linkage;

R' is hydrogen or $C_{1-4}$ alkyl;

$R^1$ is an optionally substituted hydrocarbyl group of 1 to 300 carbon atoms;

one of $R^2$ and $R^3$ is independently selected from hydrogen and optionally substituted hydrocarbyl of 1 to 10 carbon atoms, the other of $R^2$ and $R^3$ being independently selected from optionally substituted hydrocarbyl of 1 to 10 carbon atoms;

m is from 3 to 200;

n is from 0 to 20, provided that m/n is at least 1; and p is from 1 to 5.

DETAILED DESCRIPTION OF THE INVENTION

In the present invention, it is considered that the combination of features that m is at least 3 and that n is not greater than m are essential to the attainment of improved properties relative to otherwise comparable prior art compounds.

While R' may be hydrogen or a $C_{1-4}$ alkyl group, e.g. a methyl, ethyl or n-propyl group, R' is preferably a hydrogen atom.

The value of p is preferably in the range 1 to 3, advantageously 1 or 2.

The value of m is preferably from 3 to 150, more preferably 3 to 120, advantageously 3 to 50, and especially 3 to 30. Values of n from 0 to 10 are preferred. Preferably m/n is at least 2, more preferably at least 3.

As used herein, the term "hydrocarbyl" represents a radical formed by the removal of one or more hydrogen atoms from a carbon atom of a hydrocarbon(not necessarily the same carbon atom). Useful hydrocarbyls are aliphatic, acyclic or cyclic. Preferably, the hydrocarbyls are aryl, alkyl, alkenyl or cycloalkyl and are straight-chain or branched-chain. Representative hydrocarbyls include methyl, ethyl, butyl, pentyl, methylpentyl, hexenyl, ethyhexyl, dimethylhexyl, octamethylene, octenylene, cyclooctylene, methylcyclooctylene, dimethylcyclooctyl, isooctyl, dodecyl, hexadecenyl, octyl, eicosyl, hexacosyl, triacontyl and phenylethyl. When the hydrocarbyl is substituted, it contains a functional group such as carbonyl, carboxyl, nitro, tertiary amino(no N-H linkages), oxy, cyano, sufonyl and sulfoxyl. The majority of the atoms, other than hydrogen, in substituted hydrocarbyls are carbon, with the heteroatoms (e.g. oxygen, nitrogen and sulphur) representing only a minority, 33% or less, of the total non-hydrogen atoms present.

Those skilled in the art will appreciate that functional groups such as nitro and cyano in a substituted hydrocarbyl group will displace one of the hydrogen atoms of the hydrocarbyl, while functional groups such as carbonyl, carboxyl, tertiary amino (—N—), oxy, sulfonyl and sulfoxyl in a substituted hydrocarbyl group will displace a —CH— or —CH$_2$— moiety of the hydrocarbyl. In "optionally substituted hydrocarbyl of 1 to 300 carbon atoms", "1 to 300 carbon atoms" represents the total number of carbon atoms in the optionally substituted hydrocarbyl group. The same applies to "optionally substituted hydrocarbyl" of lower numbers of specified carbon atoms.

In derivatives of general formula I wherein p is 1, $R^1$ may contain one or more, e.g. 1 to 3, substituents of formula IV:

or one or more, e.g. 1 to 3, substituents of formula V:

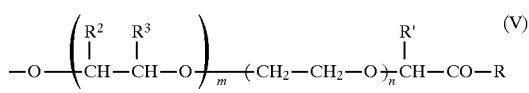

wherein R, $R^1$, $R^2$, $R^3$, m and n are as defined above in relation to formula I, subject to the total number of carbon atoms in $R^1$ being not more than 300.

Thus, for example $R^1$ may be of the formula:

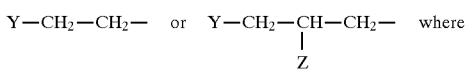

Y is of formula IV or V above and Z is of formula IV or V above.

$R^1$ is preferably a hydrocarbyl group of 1 to 300 carbon atoms, more preferably a hydrocarbyl group of 1 to 100 carbon atoms. When $R^1$ is hydrocarbyl of a relatively high number of carbon atoms, i.e. greater than about 50 carbon atoms, $R^1$ may conveniently be a polymeric hydrocarbyl such as polyisobutylene, polybutene, polypropylene or polyalphaolefin. In particularly preferred derivatives of formula I, $R^1$ represents a $C_{1-20}$ alkyl group, a phenyl or benzyl group or a ($C_{1-15}$ alkyl) phenyl or ($C_{1-15}$ alkyl) benzyl group. $R^1$ may very conveniently represent a $C_{10-18}$ alkyl group, e.g. a $C_{12-15}$ alkyl group.

Preferably, one of $R^2$ and $R^3$ is independently selected from hydrogen and hydrocarbyl of 1 to 10, preferably 1 to 4 carbon atoms, the other of $R^2$ and $R^3$ being independently selected from hydrocarbyl of 1 to 10, preferably 1 to 4, carbon atoms. Conveniently, one of $R^2$ and $R^3$ is hydrogen, the other being hydrocarbyl, preferably a $C_{1-3}$ alkyl group. Preferably, one of $R^2$ and $R^3$ is hydrogen and the other is a methyl or ethyl group, the moieties —$CHR^2$—$CHR^3$—O— then being derived from propylene oxide and/or butylene oxide (1,2-epoxybutane). When the moieties —$CHR^2$—$CHR^3$—O— contain two or more different $R^2$ and/or $R^3$ groups, the moiety —($CHR^2$—$CHR^3$—O$)_m$— may represent a block copolymeric group or a random copolymeric group. Derivatives of formula I wherein one of $R^2$ and $R^3$ is hydrogen and the other is a methyl group have been found to be very suitable.

The amines, aminoalcohols and polyols of which R in formula I represents the residue are known in the art or may be prepared by analogous methods to those used for preparing the known amines, aminoalcohols and polyols. For example, various amines and their preparation are described in U.S. Pat. No. 3,275,554, U.S. Pat. No. 3,438,757, U.S. Pat. No. 3,454,555, U.S. Pat. No. 3,565,804, U.S. Pat. No. 3,755,433 and U.S. Pat. No. 3,822,209, each incorporated herein by reference. Complex amines such as "Starburst" (trade mark) dendrimers may be used, e.g. the compound of formula $[CH_2N((CH_2)_2CONH(CH_2)_2]_2$ .

Examples of polyols include ethylene glycol, glycerol, trimethylolethane, trimethylolpropane, 1,2-butanediol, 2,3-hexanediol, 2,4-hexanediol, pinacol, erythritol, arabitol, sorbitol, mannitol, pentaerythritol, dipentaerythritol and tripentaerythritol.

Preferred derivatives of formula I are those wherein the compound of R(H)p, of which R represents the residue, has the general formula II:

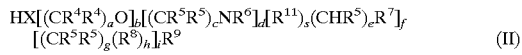

$$HX[(CR^4R^4)_aO]_b[(CR^5R^5)_cNR^6]_d[R^{11}]_s(CHR^5)_eR^7]_f \\ [(CR^5R^5)_g(R^8)_h]_rR^9 \qquad (II)$$

wherein X is 0 or $NR^6$, each $R^4$ independently represents hydrogen, hydrocarbyl of 1 to 10 carbon atoms or hydrocarbyl of 1 to 10 carbon atoms substituted by at least one hydroxy group, each $R^5$ independently represents hydrogen or hydrocarbyl of 1 to 10 carbon atoms, each $R^6$ independently represents hydrogen or hydrocarbyl of 1 to 10 carbon atoms, $R^7$ represents a $C_{5-7}$ cycloalkanediyl-NH— or 1,4-piperazinediyl moiety optionally substituted by one or more hydrocarbyl groups of 1 to 10 carbon atoms, each $R^8$ independently represents $NR^{10}$ or $CHR^{10}$, $R^9$ represents hydrogen, hydrocarbyl of 1 to 30 carbon atoms or a —$CO(CHOH)_i(CR^5R5)_j(NR^5)_k(CR^5R^5)_l$OH group, $R^{10}$ represents a —$(CR^5R^5)_rNR^6R^9$ group, $R^{11}$ represents a $C_{5-7}$ cycloalkanediyl moiety optionally substituted by one or more hydrocarbyl groups of 1 to 10 carbon atoms, a is 1 to 10,
b is 0 to 10,
c is 1 to 10,
d is 0 to 10,
e is 1 to 10,
f is 0 or 1,
g is 1 to 10,
h is 0 or 1
i is 0 to 10
j is 1 to 10,
k is 0 or 1,
l is 1 to 10,
r is 1 to 10,
s is 0 or 1, and
t is 0 or 1 and integers b, d, f and i indicate numbers of associated moieties present, and the various moieties $[(CR^4R^4)_aO]$, $[(CR^5R^5)_cNR^6]$, $[(CHR^5)_eR^7]$ and $[(CR^5R^5)_g(R^8)_h]$ may be in any linear order.

Preferably, in formula II X is 0 or $NR^6$, each $R^4$ independently represents hydrogen, $C_{1-4}$ alkyl or $C_{1-4}$ hydroxyalkyl, each $R^5$ independently represents hydrogen or $C_{1-4}$ alkyl, each $R^6$ represents hydrogen or methyl, $R^7$ represents a 1,4-piperazinediyl moiety or a cyclohexanediyl-NH— moiety optionally substituted by up to three methyl groups, each $R^8$ independently represents $NR^{10}$ or $CHR^{10}$, $R^9$ represents hydrogen, methyl or a —$CO(CHOH)_i(CHR^5)_j(NR^5)_k(CHR^5)_l$OH group, $R^{10}$ represents a —$(CHR^5)_rNHR^9$ group, $R^{11}$ represents a cyclohexanediyl moiety optionally substituted by up to three methyl groups, a is 1 to 5, b is 0 to 5, c is 1 to 6, d is 0 to 5, e is 1 to 5, f is 0 or 1, g is 1 to 5, h is 0 or 1, i is 0 to 5, j is 1 to 5, k is 0 or 1, l is 1 to 5, r is 1 to 5, s is 0 or 1, and t is 0 or 1.

Advantageously, X is O or NH, each $R^4$ independently represents hydrogen, methyl or hydroxymethyl, each $R^5$ independently represents hydrogen or methyl, each $R^6$ represents hydrogen or methyl, $R^7$ represents a 1,4-piperazinediyl moiety or a cyclohexanediyl-NH— moiety optionally substituted by up to 3 methyl groups, each $R^8$ independently represents $NR^{10}$ or $CHR^{10}$, $R^9$ represents hydrogen, methyl, or a $CO(CHOH)_i(CHR^5)_j(NR^5)_k(CHR^5)_l$OH group, $R^{10}$ represents a $(CHR^5)_rNHR^9$ group, a is 2 or 3, b is 0 to 3, c is 2 to 6, d is 0 to 4, e is 3, f is 0 or 1, g is 2 or 3, h is 1, i is 0 or 1, j is 1 to 4, k is 0 or 1, l is 1 to 4, r is 1 or 2, s is 0 or 1, and t is 0 or 1.

Examples of preferred such moieties R are the following: —$NHCH_2CH_2N(CH_2CH_2NH_2)_2$, —$O(CH_2C(CH_2OH)_2O)_bH$ where b is 1 to 3, preferably 1, —$NH(CH_2CH_2NH)_dH$ where d is 1 to 4, —$NHCH_2CH_2NHCH_2CH_2OH$, —$NH(CH_2)_cNH_2$, where c is 2 to 6, preferably 2 to 4, —$NH(CH_2)_3NH(CH_2)_2NH(CH_2)_3NH_2$, —$NH(CH_2CH_2O)_2CH_2CH_2NH_2$, —$NH(CH_2CH_2O)_2H$, —$NH(CH_2)_3(1,4$-piperazinediyl) $(CH_2)_3NH_2$, —$NH(1,4$-cyclohexanediyl) $CH_2(1,4$-cyclohexanediyl)$NH_2$, —$NHCH_2(1,3,3$-trimethyl-5-aminocyclohexyl), —$NH(CH_2CH_2CH_2NH)_2H$, —$NH(CH_2)_3CH(CH_2NH_2)(CH_2)_4NH_2$, —$NHCH_2CH_2N(CH_2CH_2NHCO(CH_2)_2CH(CH_3)OH)2$, —$NHCH_2CH_2N(CH_2CH_2NHCOCH(CH_3)CH_2CH_2OH)_2$, —$NHCH_2C(CH_3)_2CH_2NH_2$, —$NH(CH_2)_3N(CH_3)_2$ (all when p=1); and —$NH(CH_2CH_2NH)_3$— and —$NHCH_2CH_2N(CH_2CH_2NH_2)CH_2CH_2NH$— (when p=2).

Most preferably, R(H)p is selected from the group consisting of pentaerythritol , triethylenetetramine and tris(2-aminoethyl)amine.

The present invention further provides a process for preparing an alkoxy acetic acid derivative of general formula I as defined above which comprises reacting a compound of general formula III:

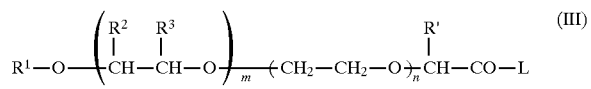

wherein R', R$^1$, R$^2$, R$^3$, m and n are as defined above and L represents a leaving group, with a compound of general formula R(H)p, wherein R is as defined above in molar ratio compound of formula III: compound of formula R(H)$_p$ of substantially p:1, optionally followed by converting the resulting acid derivative of formula I into another acid derivative of formula I with different group R as defined above.

Although the leaving group L may be, for example, a halogen atom, such as chlorine or bromine atom, L is preferably a hydroxy group.

Reaction between the compound of formula III and the compound of formula R(H)$_p$ may conveniently be effected in the presence of an inert solvent, e.g. an aromatic hydrocarbon such as toluene or xylene.

When L is a hydroxy group, the reaction may conveniently be effected at a temperature in the range from 100° C. to the reflux temperature of the reaction mixture. Water may advantageously be removed, e.g. by means of a Dean-Stark extractor and condenser. When R(H)$_p$ is a polyol, advantageously an acid, such as para-toluene sulphonic acid, is present.

Conversion of one R group into a different R group as defined above is most likely to be done when the desired final product of formula I as defined above contains one or more R$^9$ moieties, wherein R$^9$ is a —CO(CHOH)$_i$(CHR$^5$)$_j$(NR$^5$)$_k$(CHR$^5$)$_l$OH group. For example, a compound of formula I wherein R$^9$ is hydrogen may be converted into a compound of formula I wherein R$^9$ is a CO(CH$_2$)$_2$CH(CH$_3$)OH group, a COCH$_2$N(CH$_3$)CH$_2$CH$_2$OH group or a CO(CHOH)C(CH$_3$)$_2$CH$_2$OH group respectively by reaction with gamma-valerolactone, N-methylmorpholinone or pantolactone.

Compounds of formula III as defined above wherein L is other than a hydroxy group can be prepared in known manner from the corresponding compound of formula III wherein L is a hydroxy group.

Compounds of formula III wherein L is a hydroxy compound may be prepared by reaction of an alpha-halo carboxylic acid of general formula VI:

$$Q-\underset{\underset{R'}{|}}{CH}-COOH \qquad (VI)$$

or an alkali metal salt thereof, wherein R' is as defined above and Q is a halogen, preferably chlorine, atom with a compound of formula VII:

where R$^1$, R$^2$, R$^3$, m and n are as defined above, in the presence of a suitable base and an inert solvent. Suitable bases include sodium and potassium hydrides and amides, for which solvents such as tetrahydrofuran and xylene are suitable, and potassium tertiary butoxide, for which tertiary butanol is suitable as solvent. In an aprotic solvent, sodium metal may be used to generate suitably basic conditions. When n is 1 to 20 (i.e. greater than 0), milder bases can be employed, such as sodium and potassium hydroxides, e.g. using toluene as solvent.

Compounds of formula VII wherein n is 1 to 20 may be generated by reacting a compound of formula VII wherein n is 0 with ethylene oxide in molar ratio compound of formula VII: ethylene oxide 1: n.

A compound of formula VII wherein n is 1 to 20 may be converted into an alkoxyacetic acid of general formula III wherein L is a hydroxy group, R' is hydrogen and n is 0 to 19 by a process similar to that described in U.S. Pat. No. 5,380,930, incorporated herein by reference. In such a process, the compound of formula VII wherein n is 1 to 20 is conveniently reacted with a stable free radical nitroxide, such as piperidine-1-oxyl, in the presence of nitric acid and an oxidising agent, e.g. air or gaseous oxygen, in the presence or absence of a solvent.

Alkoxy acetic acid derivatives of formula I may alternatively, in principle, be prepared by reacting a compound of general formula VIII:

where R' and p are as defined above and R" is R as above or a protecting group with appropriate alkylene oxides in suitable order, followed by end-capping the resulting product in order to produce the desired alkoxyacetic acid derivative of formula I, or when R" is a protecting group, with reaction with a compound R(H)$_p$ as defined above to displace the protecting group and finally obtain the desired alkoxy acetic acid derivative of formula I.

The present invention further provides a fuel composition comprising a major amount of a fuel for an internal combustion engine and a minor amount of an acid derivative of formula I as defined above, and an additive concentrate suitable for addition to fuel for an internal combustion engine which comprises a fuel-compatible diluent and an acid derivative of formula I as defined above.

The alkoxy acetic acid derivatives of formula I have useful application both in fuel compositions for spark-ignition engines (gasoline compositions) and in fuel compositions for compression ignition engines (diesel fuel compositions).

The "minor amount" referred to above is preferably less than 10% w of the composition, more preferably less than 1% w and advantageously less than 0.1% w (1000 ppmw) (parts per million by weight) of the composition. In preferred fuel compositions of the invention, the alkoxy acetic acid derivative is present in an amount in the range from about 50 to about 1000 ppmw of the fuel composition.

For gasoline compositions, the fuel will be a fuel boiling in the gasoline boiling range, and it may consist substantially of hydrocarbons or it may contain blending components. Alternatively, e.g. in countries such as Brazil, the fuel may consist substantially of ethanol.

Suitable liquid hydrocarbon fuels of the gasoline boiling range are mixtures of hydrocarbon boiling in the temperature range from about 25° C. to about 232° C., and comprise mixtures of saturated hydrocarbons, olefinic hydrocarbons and aromatic hydrocarbons. Preferred are gasoline mixtures having a saturated hydrocarbon content ranging from about 40% to about 80% by volume, an olefinic hydrocarbon content from 0% to about 30% by volume and an aromatic hydrocarbon content from about 10% to about 60% by volume. The base fuel is derived from straight run gasoline, polymer gasoline, natural gasoline, dimer and trimerized olefins, synthetically produced aromatic hydrocarbon mixtures, from thermally or catalytically reformed hydrocarbons, or from catalytically cracked or thermally cracked petroleum stocks, and mixtures of these. The hydrocarbon composition and octane level of the base fuel are not critical. The octane level, (R+M)/2, will generally be above about 85 (where R is Research Octane Number and M is Motor Octane Number).

Any conventional base gasoline can be employed in the practice of the present invention. For example, hydrocarbons in the gasoline can be replaced by up to a substantial amount of conventional alcohols or ethers, conventionally known for use in fuels. The base gasolines are desirably substantially free of water since water could impede a smooth combustion.

Normally, the gasolines to which the invention is applied may be leaded or unleaded, although are preferably substantially lead-free, and may contain minor amounts of one or more blending agents such as methanol, ethanol, tertiary butanol, ethyl tertiary butyl ether, methyl tertiary butyl ether, and the like, at from about 0.1% by volume to about 25% by volume of the base fuel, although larger amounts (e.g. up to 40% v) may be utilized. The gasolines can also contain conventional additives including antioxidants such as phenolics, e.g. 2,6-di-tert-butylphenol or phenylenediamines, e.g. N,N'-di-sec-butyl-p-phenylenediamine, dyes, metal deactivators, dehazers such as polyester-type ethoxylated alkylphenol-formaldehyde resins. Corrosion inhibitors, such as that commercially sold by Rhein Chemie, Mannheim, Germany as "RC 4801", or a polyhydric alcohol ester of a succinic acid derivative having on at least one of its alphacarbon atoms an unsubstituted or substituted aliphatic hydrocarbon group having from 20 to 500 carbon atoms, for example, pentaerythritol diester of polyisobutylene-substituted succinic acid, the polyisobutylene group having an average molecular weight of about 950, in an amount from about 1 ppmw to about 1000 ppmw, may also be present. The fuels can also contain antiknock compounds such as methyl cyclopentadienylmanganese tricarbonyl, tetraethyl lead or other lead-containing compounds, and ortho-azodiphenol as well as co-antiknock compounds such as benzoyl acetone.

A preferred gasoline composition of the invention may additionally contain a minor amount of at least one additional additive compound selected from the group consisting of polyalkenyl amines, Mannich amines, polyalkenyl succinimide, poly(oxyalkylene)amines, poly(oxyalkylene) carbamates, and poly(alkenyl)-N-substituted carbamates.

An effective amount of one or more acid derivatives of formula I are introduced into the combustion zone of the engine in a variety of ways to prevent build-up of deposits, or to accomplish the reduction of intake valve deposits or the modification of existing deposits that are related to octane requirement. As mentioned, a preferred method is to add a minor amount of one or more acid derivatives of formula I to the gasoline. For example, one or more acid derivatives of formula I are added directly to the gasoline or are blended with one or more carriers and/or one or more hydrocarbon-soluble alkali metal or alkaline earth metal salts and/or one or more additional detergents before being added to the gasoline.

The amount of acid derivative of formula I used will depend on the particular variation of formula I used, the engine, the fuel, and the presence or absence of carriers, additional detergents and diluents.

The carrier, when utilized, may conveniently have an average molecular weight from about 250 to about 5000. Suitable carriers, when utilized, include hydrocarbon based materials such as polyisobutylenes (PIB's), polypropylenes (PP's) and polyalphaolefins (PAO's), all of which may be hydrogenated or unhydrogenated but are preferably hydrogenated; polyether based materials such as polybutylene oxides (poly BO's), polypropylene oxides (poly PO's), polyhexadecene oxides (poly HO's) and mixtures thereof (i.e. both (poly BO)+(poly PO) and poly-BO-PO)); and mineral oils such as those sold by member companies of the Royal Dutch/Shell group under the designations "HVI" and "XHVI" (trade mark), Exxon Naphthenic 900 sus mineral oil and high viscosity index oils in general. The carrier is preferably selected from PIB's, poly BO's and poly PO's with poly PO's being the most preferred.

A particularly prepared carrier fluid comprises a combination of a polyalphaolefin having a viscosity at 100° C. in the range $2 \times 10^{-6}$ to $2 \times 10^{-5}$ m$^2$/s (2 to 20 centistokes) being a hydrogenated oligomer containing 18 to 80 carbon atoms derived from at least one alphaolefinic monomer containing from 8 to 16 carbon atoms, and a polyoxyalkylene compound selected from glycols, mono- and diethers thereof, having number average molecular weight ($M_n$) in the range 400 to 3000, the weight ratio polyalphaolefin: polyoxyalkylene compound being in the range 1:10 to 10:1.

The polyalphaolefins are primarily trimers, tetramers and pentamers, and synthesis of such materials is outlined in Campen et al., "Growing use of synlubes", Hydrocarbon Processing, February 1982, pages 75 to 82. The polyalphaolefin is preferably derived from an alphaolefinic monomer containing from 8 to 12 carbon atoms. Polyalphaolefins derived from decene-1 have been found to be very effective. The polyalphaolefin preferably has viscosity at 100° C. in the range of $6 \times 10^{-6}$ to $1 \times 10^{-5}$ m$^2$/s (6 to 10 centistokes). Polyalphaolefin having a viscosity at 100° C. of $8 \times 10^{-6}$ m$^2$/s (8 centistokes) has been found to be very effective.

Preferred polyoxyalkylene compounds for use in combination with these polyalphaolefins are described in EP-A-588429, incorporated herein by reference.

The carrier concentration in the final fuel composition is up to about 1000 ppm weight. When a carrier is present, the preferred concentration is from about 50 ppm by weight to about 400 ppm by weight, based on the total weight of the fuel composition. Once the carrier is blended with one or more compounds of formula I and any other desired components, the blend is added directly to the fuel or packaged for future use.

The hydrocarbon-soluble alkali metal or alkaline earth metal salt, when utilized, may be one of those described in WO 87/01126, and the compounds of formula I are particularly suitable for incorporation, as additional component, in fuel compositions as described in WO 87/01126, incorporated herein by reference. Preferred hydrocarbon-soluble alkali metal or alkaline earth metal salts are, however, alkali metal or alkaline earth metal salts of a succinic acid derivative. Such a salt of a succinic acid derivative, when utilized, will have as a substituent on one of its alpha-carbon atoms an unsubstituted or substituted aliphatic hydrocarbon group having from 20 to 200 carbon atoms. Alternatively, the succinic acid derivative will have as a substituent on one of its alpha-carbon atoms an unsubstituted or substituted hydrocarbon group having from 20 to 200 carbon atoms which is connected to the other alpha-carbon atom by means of a hydrocarbon moiety having from 1 to 6 carbon atoms, forming a ring structure. Suitable such salts are described for example in EP-A-207560 and in EP-A-491439, incorporated herein by reference.

The salts of the succinic acid derivative can be monobasic or dibasic. Monobasic salts in which the remaining carboxylic acid group has been transformed into an amide or ester group may also be used. Suitable alkali metal salts of a partial ester of an alkyl polyether alcohol with a succinic acid derivative are described in EP-A-491439, incorporated herein by reference.

Suitable metal salts include lithium, sodium, potassium, rubidium, caesium and calcium salts. Particularly preferred salts are described in EP-A-207560, incorporated herein by reference.

The aliphatic hydrocarbon substituent(s) of the succinic acid derivative is suitably derived from a polyolefin, the monomers of which have 2 to 6 carbon atoms. Thus, convenient substituents include polyethylene, polypropylene, polybutylenes, polypentenes, polyhexenes or mixed polymers. Particularly preferred is an aliphatic hydrocarbon group which is derived from polyisobutylene.

The hydrocarbon group may include an alkyl and/or an alkenyl moiety and may contain substituents. One or more hydrogen atoms may be replaced by another atom, for example halogen, or by a non-aliphatic organic group, e.g. an (un)substituted phenyl group, a hydroxy, ether, ketone, aldehyde or ester. A very suitable substituent in the hydrocarbon group is at least one other metal succinate group, yielding a hydrocarbon group having two or more succinate moieties.

The aliphatic hydrocarbon group should contain 20 to 200, preferably 35–150, carbon atoms. When a polyolefin is used as substituent the chain length is conveniently expressed as the number average molecular weight. The number average molecular weight of the substituent, e.g. determined by osmometry, is advantageously from 400 to 2000.

The succinic acid derivative may have more than one $C_{20-200}$ aliphatic hydrocarbon group attached to one or both alpha-carbon atoms, but preferably it has one $C_{20-200}$ aliphatic hydrocarbon group on one of its alpha-carbon atoms and on the other alphacarbon atom either no substituent or a hydrocarbon of only a short chain length, e.g. $C_{1-6}$ group. The latter group can be linked with the $C_{20-200}$ hydrocarbon group forming a ring structure.

The gasoline compositions of the present invention may also contain one or more additional detergents. When additional detergents are utilized, the gasoline composition will comprise a mixture of a major amount of hydrocarbons in the gasoline boiling range as described hereinbefore, a minor amount of one or more compounds of formula I as described hereinbefore and a minor amount of an additional detergent selected from polyalkenyl amines, e.g. polybutyleneamines, such as "KEROCOM" polyisobutyleneamine, available ex. BASF, Mannich amines, polyalkenyl succinimides, poly (oxyalkylene)amines, poly(oxyalkylene) carbamates, poly (alkenyl)-N-substituted carbamates, and mixtures thereof. As noted above, a carrier as described hereinbefore may also be included. The "minor amount" is preferably less than about 10% by weight of the total fuel composition, more preferably less than about 1% by weight of the total fuel composition and yet more preferably less than about 0.1% by weight of the total fuel composition.

The polyalkenyl amine detergents utilised comprise at least one monovalent hydrocarbon group having at least 50 carbon atoms and at least one monovalent hydrocarbon group having at most five carbon atoms bound directly to separate nitrogen atoms of a diamine. Preferred polyalkenyl amines are polyisobutenyl amines. Polyisobutenyl amines are known in the art and representative examples are disclosed in various U.S. patents including U.S. Pat. No. 3,753,670, U.S. Pat. No. 3,756,793, U.S. Pat. No. 3,574,576 and U.S. Pat. No. 3,438,757, each incorporated herein by reference. Particularly preferred polyisobutenyl amines for use in the present fuel composition include N-polyisobutenyl-N', N'-dimethyl-1,3-diaminopropane (PIB-DAP), OGA-472 (a polyisobutenyl ethylene diamine available commercially from Oronite), N-polyisobutenyl diethylene triamine (PIB-DETA) and N-polyisobutenyl triethylene tetramine (PIB-TETA).

The Mannich amine detergents utilised comprise a condensation product of a high molecular weight alkyl-substituted hydroxyaromatic compound, an amine which contains an amino group having at least one active hydrogen atom (preferably a polyamine), and an aldehyde. Such Mannich amines are known in the art and are disclosed in U.S. Pat. No. 4,231,759, incorporated herein by reference. Preferably, the Mannich amine is an alkyl substituted Mannich amine.

The polyalkenyl succinimide detergents comprise the reaction product of a dibasic acid anhydride with either a polyoxyalkylene diamine, a hydrocarbyl polyamine or mixtures of both. Typically the succinimide is substituted with the polyalkenyl group but the polyalkenyl group may be found on the polyoxyalkylene diamine or the hydrocarbyl polyamine. Polyalkenyl succinimides are also known in the art and representative examples are disclosed in various patent references including U.S. Pat. No. 3,443,918, EP-A-208560, DE-OLS 3,126,404, U.S. Pat. No. 4,234,435, U.S. Pat. No. 4,810,261, U.S. Pat. No. 4,852,993, U.S. Pat. No. 4,968,321, U.S. Pat. No. 4,985,047, U.S. Pat. No. 5,061,291 and U.S. Pat. No. 5,147,414, each incorporated herein by reference.

Particularly effective succinimide detergents are those obtained by reacting at least one amine, with a polyalkenyl derivative of a monoethylenically unsaturated $C_{4-10}$ dicarboxylic acid material in which the ratio of dicarboxylic acid moieties per polyalkenyl chain is not greater than 1.2:1 and the number average molecular weight (Mn) of the polyalkenyl chain is in the range from 1600 to 5000, e.g. as described in EP-A-587250, incorporated herein by reference.

Amines employed in the preparation of said succinimide detergents are preferably $C_{1-30}$, more preferably $C_{1-18}$, and especially $C_{8-12}$, amines containing 1 to 8 nitrogen atoms. Such amines may be branched or unbranched, saturated aliphatic, primary or secondary amines, containing 1 to 8 nitrogens, preferably mono- or diamines, such as ethylamine, butylamine, sec. butylamine, diethylamine and 3-dimethylamino-1-propylamine, but including higher polyamines such as alkylene polyamines, wherein pairs of nitrogen atoms are joined by alkylene groups of 2 to 4 carbon atoms.

Poly(oxyalkylene)amines are described, for example, in U.S. Pat. No. 4,985,047 and U.S. Pat. No. 4,332,595, in EP-A-440 248, EP-A-310 875, EP-A-208 978 and WO-A-85 01956, each incorporated herein by reference. The poly (oxyalkylene) carbamate detergents comprise an amine moiety and a poly(oxyalkylene) moiety linked together through a carbamate linkage, i.e.,

$$\text{—O—C(O)—N—} \qquad (IX)$$

These poly(oxyalkylene) carbamates are known in the art and representative examples are disclosed for example in U.S. Pat. No. 4,191,537, U.S. Pat. No. 4,160,648, U.S. Pat. No. 4,236,020, U.S. Pat. No. 4,270,930, U.S. Pat. No. 4,288,612 and U.S. Pat. No. 4,881,945, each incorporated herein by reference. Particularly preferred poly (oxyalkylene) carbamates for use in the present fuel composition include OGA-480 (a poly(oxyalkylene) carbamate which is available commercially from Oronite).

The poly(alkenyl)-N-substituted carbamate detergents utilised are of the formula:

$$R-A-\underset{\underset{O}{\|}}{C}-OR^1 \quad (X)$$

in which R is a poly(alkenyl) chain; $R^1$ is a hydrocarbyl or substituted hydrocarbyl group; and A is an N-substituted amino group. Poly(alkenyl)-N-substituted carbamates are known in the art and are disclosed in U.S. Pat. No. 4,936,868, incorporated herein by reference.

The one or more additional detergents are added directly to the fuel boiling in the gasoline boiling range, blended with one or more carriers, blended with one or more acid derivatives of formula I, or blended with one or more acid derivatives of formula I and one or more carriers before being added to the fuel.

The concentration of the one or more additional detergents in the final fuel composition is generally up to about 1000 ppmw for each additional detergent. When one or more additional detergents are utilised, the preferred concentration for each additional detergent is from about 10 ppmw to about 400 ppmw, based on the total weight of the fuel composition, even more preferably from about 25 ppmw to about 250 ppmw, based on the total weight of the fuel composition.

Additive components can be added separately to the gasoline or can be blended with one or more diluents, forming an additive concentrate, and added to the gasoline together. Suitable gasoline-compatible diluents are hydrocarbons and mixtures of hydrocarbons with alcohols or ethers, such as methanol, ethanol, propanol, 2-butoxyethanol, methyl tert-butyl ether, or higher alcohols such as "Dobanol 91", (Trade Mark) available from member companies of the Royal Dutch/Shell group.

Preferably the diluent is an aromatic hydrocarbon solvent such as toluene, xylene, mixtures thereof or mixtures of toluene or xylene with an alcohol. Additionally preferred diluents include "Shellsol AB", "Shellsol R", (Trade Marks) and low aromatic white spirit (LAWS), which are available from member companies of the Royal Dutch/Shell group.

For diesel fuel compositions, the fuel will be a diesel oil, which may be a hydrocarbon fuel (a middle distillate fuel oil), which may be a conventional fuel or a low-sulphur fuel having a sulphur concentration below 500 ppmw, preferably below 50 ppmw, advantageously below 10 ppmw. Diesel fuels typically have initial distillation temperature about 160° C. and 90% point of 290°–360° C., depending on fuel grade and use. Vegetable oils may also be used as diesel fuels per se or in blends with hydrocarbon fuels.

Low-sulphur fuels will typically require a lubricity additive to reduce fuel pump wear.

Additive concentrates suitable for incorporating in diesel fuel compositions will contain the acid derivative of formula I and a fuel-compatible diluent, which may be a non-polar solvent such as toluene, xylene, white spirits and those sold by member companies of the Royal Dutch/Shell Group under the Trade Mark "SHELLSOL", and/or a polar solvent such as esters and , in particular, alcohols, e.g. hexanol, 2-ethylhexanol, decanol, isotridecanol and alcohol mixtures such as those sold by member companies of the Royal Dutch/Shell Group under the Trade Mark "LINEVOL", especially "LINEVOL" 79 alcohol which is a mixture of $C_{7-9}$ primary alcohols, or the $C_{12-14}$ alcohol mixture commercially available from Sidobre Sinnova, France under the Trade Mark "SIPOL".

Additive concentrates and diesel fuel compositions prepared therefrom may additionally contain additional additives such as low molecular weight amine co-detergents, dehazers, e.g. alkoxylated phenol formaldehyde polymers such as those commercially available as "NALCO" (Trade Mark) 7D07 (ex. Nalco), and "TOLAD" (Trade Mark) 2683 (ex. Petrolite; anti-foaming agents (e.g. the polyether-modified polysiloxanes commercially available as "TEGOPREN" (Trade Mark) 5851, Q 25907 (ex. Dow Corning) or "RHODORSIL" (Trade Mark) (ex. Rhone Poulenc)); ignition improvers (e.g. 2-ethylhexyl nitrate, cyclohexyl nitrate, di-tertiary-butyl peroxide and those disclosed in US Patent No. 4,208,190 at Column 2, line 27 to Column 3, line 21) incorporated herein by reference; anti-rust agents (e.g. that commercially sold by Rhein Chemie, Mannheim, Germany as "RC 4801", or polyhydric alcohol esters of a succinic acid derivative, the succinic acid derivative having on at least one of its alpha-carbon atoms an unsubstituted or substituted aliphatic hydrocarbon group containing from 20 to 500 carbon atoms, e.g. the pentaerythritol diester of polyisobutylene-substituted succinic acid), reodorants, anti-wear additives; anti-oxidants (e.g. phenolics such as 2,6-di-tert-butylphenol, or phenylenediamines such as N,N'-di-sec-butyl-p-phenylenediamine), metal deactivators and lubricity agents (e.g. those commercially available as EC831 (ex. Paramins) or "HITEC" (Trade Mark) 580 (ex. Ethyl Corporation)).

Preferred low molecular weight amine co-detergents are $C_{10-20}$ alkylamines. Aliphatic primary monoamines, particularly linear aliphatic primary monoamines, having 10 to 20 carbon atoms are particularly preferred. The alkylamine preferably has 10 to 18, e.g. 12 to 18, more preferably 12 to 16 carbon atoms. Dodecylamine is particularly preferred.

Unless otherwise stated, the (active matter) concentration of each additive in the diesel fuel is preferably up to 1 percent by weight more preferably in the range from 5 to 1000 ppmw (parts per million by weight of the diesel fuel). The (active matter) concentration of the compound of formula I in the diesel fuel is preferably 50 to 1000 ppmw.

The (active matter) concentration of the dehazer in the diesel fuel is preferably in the range from 1 to 20, more preferably from 1 to 15, still more preferably from 1 to 10 and advantageously from 1 to 5 ppmw. The (active matter) concentrations of other additives (with the exception of the ignition improver and the lubricity agent) are each preferably in the range from 0 to 20, more preferably from 0 to 10 and advantageously from 0 to 5 ppmw. The (active matter) concentration of the ignition improver in the diesel fuel is preferably in the range from 0 to 600 and more preferably from 0 to 500 ppmw. If an ignition improver is incorporated into the diesel fuel, it is conveniently used in an amount of 300 to 500 ppmw. If a lubricity agent is incorporated into the diesel fuel, it is conveniently used in an amount of 100 to 500 ppmw.

The diesel oil itself may be an additised (additive-containing) oil or an unadditised (additive-free) oil. If the diesel oil is an additised oil, it will contain minor amounts of one or more additives, e.g. one or more additives selected from anti-static agents, pipeline drag reducers, flow improvers (e.g. ethylene/vinyl acetate copolymers or acrylate/maleic anhydride copolymers) and wax anti-settling agents (e.g. those commercially available under the Trade Marks "tPARAFLOW" (e.g. "PARAFLOW" 450; ex. Paramins), "OCTEL" (e.g. "OCTEL" W 5000; ex. Octel) and "DODIFLOW" (e.g. "DODIFLOW" V 3958; ex. Hoechst).

The present invention still further provides a method of operating an internal combustion engine (e.g. a spark-ignition engine or a compression-ignition engine) which comprises introducing into the combustion chambers of said engine a fuel composition (e.g. a gasoline composition or diesel fuel composition, as appropriate) as defined above.

Use of alkoxy acetic acid derivatives of formula I as additives in fuels for internal combustion engines may result in attaining one or more of a number of effects such as inlet system cleanliness (intake valves, fuel injectors, carburettors), combustion chamber cleanliness (in each case either or both of keep clean and clean-up effects), anti-corrosion (including anti-rust) and reduction or elimination of valve-stick.

The invention will be further understood from the following illustrative examples which are included for illustrative purposes only and are no way intended to limit the scope of the present invention.

EXAMPLES

In the following examples, Examples I to V relate to the preparation of intermediate acids, and Examples 1 to 24 to compounds of formula I. In the examples, various polyether starting material of the general formula:

(Q)

wherein $R^1$ represents a $C_{12-15}$ alkyl group are designated as follows:

Polyether A is a polyoxypropylene glycol hemiether (monoether) corresponding to formula Q wherein m is in the range 17 to 23 and n is 0, prepared using a mixture of $C_{12-15}$ alcohols as initiator, and having $M_n$ in the range 1200 to 1500 and a kinematic viscosity in the range 72 to 82 mm$^2$/s at 40° C. according to ASTM D 445, available under the trade designation "SAP 949" from member companies of the Royal Dutch/Shell group;

Polyether B is a polyoxypropylene glycol hemiether (monoether) corresponding to formula Q wherein m is in the range 3.5 to 5.5 and n is 0, prepared using a mixture of $C_{12-15}$ alkanols as initiator, and having $M_n$ in the range 435 to 505 and a kinematic viscosity in the range 16 to 21 mm$^2$/s at 40° C. according to ASTM D 445, available under the trade designation "OXILUBE 500" ("OXILUBE" is a registered trade mark) from member companies of the Royal Dutch/Shell group;

Polyether C is a polyoxypropylene glycol hemiether (monoether) corresponding to formula Q wherein m is about 120 and n is 0, prepared using a mixture of $C_{12-15}$ alkanols as initiator, having a hydroxyl value of 0.14 milliequivalents per gram according to ASTM D 4274-88 and $M_n$ calculated therefrom (on the basis of one hydroxyl group per molecule) of 7150, and a kinematic viscosity in the range of 2300 to 2400 mm$^2$/s at 40° C. according to ASTM D 445;

Polyether D is a polyalkylene glycol hemiether (monoether) corresponding to formula Q wherein m is 19 and n is 5, prepared by reacting a sample of Polyether A with ethylene oxide in molar ratio 1:5 in the presence of potassium hydroxide as base, at 125° C., under pressure. Polyether D had hydroxyl value of 0.625 milliequivalents per gram according to ASTM D 4274-88 and a kinematic viscosity of 98.3 mm$^2$/s at 40° C according to ASTM D 445.

Various abbreviations are employed in the examples as follows:

"AV" denotes acid value, and this was determined using a "Metrohm 670" (trademark) potentiometric titrometer according to a method based upon ASTM D 664-89 with modified solvent system (75% w toluene, 12.5% w acetonitrite, 12.5% w acetic acid);

"TBN" denotes total basic nitrogen, and this was determined using a "Metrohm 670" (trade mark) potentiometric titrometer according to a method based upon ASTM D 2896 with modified solvent system (75% w toluene, 12.5% w acetonitrile, 12.5% w acetic acid);

"AM" denotes active matter content, and this was determined by separating inactive material from the desired active matter in obtained product on a silica column using hexane as eluant, and is expressed as a percentage relative to the obtained product.

"meqg$^{-1}$" denotes milliequivalents per gram.

In the examples and tests which follow, all parts and percentages are by weight unless stated otherwise, and temperatures are in degrees Celsius.

Intermediate acids, in the form of alkoxy acetic acids derivatives of general formula:

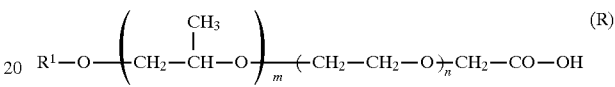
(R)

wherein $R^1$ represents a $C_{12-15}$ alkyl group, were prepared from the above polyether starting materials as follows:

Example I

Preparation of alkoxy acetic acid A (m=17 to 23, n=0)

To a 3000 ml flask, equipped with mechanical stirrer and nitrogen purge, was added sodium hydride (88 g, 2.2 mol, 60% dispersion in oil) and tetrahydrofuran (500 ml). To the resulting agitated mixture, a solution of Polyether A (1500 g, 1 mol) in tetrahydrofuran (1500 ml) was added, gradually over a period of approximately 3 hours. The mixture was then heated to reflux, with stirring, for 3 hours, cooled to 40°–50° C. and a solution of chloroacetic acid (94.5 g, 1 mol) in tetrahydrofuran (100 ml) was added over approximately 2 hours. The reaction mixture was heated to reflux for 3 hours, cooled to ambient temperature (20° C.) and then acidified with hydrochloric acid (2N aqueous solution) (addition continued until sufficient to render the mixture acidic). The reaction mixture was extracted with diethylether (3×1 L) and the combined organic phase was washed with water (3×1 L). The organic phase was dried over MgSO$_4$, filtered and evaporated to afford the desired product as 1560 g of a pale yellow oil, AV=0.596 meqg$^{-1}$, AM=85.5%.

This product was also prepared by variations of this process in which ethylchloroacetate or sodium chloroacetate were used instead of chloroacetic acid, wherein tertiary butanol or xylene were used as solvent instead of tetrahydrofuran and wherein potassium tertiary butoxide, sodamide or sodium metal (with xylene as solvent) were used instead of sodium hydride.

Example II

Preparation of alkoxy acetic acid B (m=3.5 to 5.5, n=0)

To a 3000 ml flask, equipped with mechanical stirrer and nitrogen purge, was added sodium hydride (88 g, 2.2 mol, 60% dispersion in oil) and tetrahydrofuran (500 ml). To this agitated mixture, a solution of Polyether B (555 g, 1 mol) in tetrahydrofuran (1000 ml) was added, gradually over a period of approximately 3 hours. The mixture was stirred, for 3 hours and a solution of chloroacetic acid (108 g, 1.1 mol) in tetrahydrofuran (500 ml) was added over approximately 4 hours. The reaction mixture was heated to reflux for 14 hours, cooled and then acidified with hydrochloric acid (2N aqueous solution). The reaction mixture was extracted with diethylether (3×1 L) and the combined organic phase was washed with water (3×1 L). The organic phase was dried over Na$_2$SO$_4$, filtered and evaporated to afford the desired product as 604 g of a pale yellow oil, AV=1.72 meqg$^{-1}$.

Example III

Preparation of alkoxy acetic acid C (m=120, n=0)

To a 2000 ml flask, equipped with mechanical stirrer and nitrogen purge, was added sodium hydride (8.8 g, 0.22 mol, 60% dispersion in oil) and tetrahydrofuran (250 ml). This mixture was heated to reflux, with stirring, and a solution of Polyether C (460 g, 0.1 mol) in tetrahydrofuran (1000 ml) added dropwise over 2 hours. After 3 hours a solution of chloroacetic acid (10.4 g, 0.11 mol) in tetrahydrofuran (50 ml) was added and the mixture maintained under reflux, with stirring, for a further 4 hours. The mixture was cooled, acidified with hydrochloric acid (2N aqueous solution) and extracted with ether (3×750 ml). The combined organic phase was washed with saturated aqueous sodium chloride solution (3×200 ml), dried over MgSO$_4$, filtered and evaporated to afford 452 g of the desired product as a pale yellow oil, AV=0.25 meqg$^{-1}$.

Example IV

Preparation of alkoxy acetic acid D (m=19, n=5)

To a 500 ml flask equipped with Dean-Stark extractor and condenser, was added Polyether D (150 g, 0.09 mol), toluene (250 ml) and a solution of sodium hydroxide (3.6 g, 0.1 mol) in water (20 ml). The mixture was heated at reflux temperature until all the water from the reaction mixture had been removed through the Dean-Stark extractor. The mixture was cooled sufficiently to allow the addition of the sodium salt of chloroacetic acid (11.6 g, 0.1 mol) and the mixture heated under reflux for 14 hours. The mixture was cooled, acidified with hydrochloric acid (2N aqueous solution) and the phases separated. The organic phase was washed with saturated aqueous sodium chloride solution (2×50 ml), dried over MgSO$_4$, filtered and evaporated to afford the desired product as 149 g of a pale yellow oil, AV=0.23 meqg$^{-1}$.

This product was also prepared by variations of this process wherein aqueous potassium hydroxide solution or potassium hydroxide pellets were used instead of aqueous sodium hydroxide solution, and wherein chloroacetic acid was used instead of the sodium salt of chloroacetic acid.

Example V

Preparation of alkoxy acetic acid E(m=19, n=4)

To a round-bottomed flask equipped with magnetic stirrer was added Polyether D (12 g), dichloromethane (25 ml), nitric acid (69%, 1 ml) and 2,2,6,6-tetramethylpiperidine-1-oxyl (0.3 g, 2.5% w/w, based on Polyether D). The resulting mixture was stirred at 35° C. while oxygen was bubbled through at a rate of 30 ml/minute for 3 hours at ambient pressure. The mixture was then cooled to ambient temperature (20° C.), washed with brine (3×50 ml), dried over MgSO$_4$, filtered and evaporated to afford the desired product as 10.4 g of a pale yellow oil, AV=0.41 meqg$^{-1}$.

This product was also prepared by variations of this process in which 4-hydroxy-2,2,6,6-tetramethylpiperidine-1-oxyl or 4-acetamido-2,2,6,6-tetramethylpiperidine-1-oxyl were used instead of 2,2,6,6-tetramethylpiperidine-1-oxyl, wherein air was used instead of gaseous oxygen and in the absence of dichloromethane (solvent).

Alkoxy acetic acid derivations of general formula:

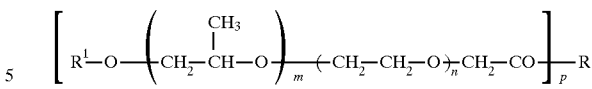

wherein R$^1$ represents a C$_{12-15}$ alkyl group, were prepared from the above intermediate acids as follows:

Example 1

(m=17 to 23, n=0, p=1, R=—NH CH$_2$CH$_2$N(CH$_2$CH$_2$NH$_2$)$_2$)

To a three litre flask, equipped with mechanical stirrer, Dean-Stark extractor and condenser, was added alkoxy acetic acid A (1405 g, 0.9 mol), toluene (1500 ml) and tris(2-aminoethyl)amine (123.1 g, 0.84 mol). The resulting mixture was heated to reflux temperature and maintained at that temperature, with stirring, for 16 hours while removing water evolved from the reaction mixture. The reaction mixture was then evaporated under high vacuum to afford the desired product as 1446 g of a pale brown oil, TBN= 1.76%N, AM=89.7%.

Example 2

(m=120, n=0, p=1, R=—NH CH$_2$CH$_2$N(CH$_2$CH$_2$NH$_2$)$_2$)

To a 500 ml flask, equipped with magnetic stirrer, Dean-Stark extractor and condenser, was added alkoxy acetic acid C (150 g, 0.03 mol), xylene (250 ml) and tris(2-aminoethyl)amine (5.5 g, 0.038 mol). The resulting mixture was heated to reflux temperature and maintained at that temperature, with stirring, for 8 hours while removing water evolved from the reaction mixture. The resulting mixture was evaporated, dissolved in heptane (250 ml), washed with sodium chloride solution (2×100 ml, saturated), dried over MgSO$_4$, filtered and evaporated under high vacuum to afford the desired product as 133 g of a pale brown oil, TBN=0.27% N, AM=83.3%.

Example 3

(m=17 to 23, n=0, p=1, R=—NH—(CH$_2$CH$_2$NH)$_2$H)

To a 500 ml flask, equipped with magnetic stirrer, Dean-Stark extractor and condenser, was added alkoxy acetic acid A (115 g, 0.07 mol), xylene (250 ml) and diethylenetriamine (7.3 g, 0.07 mol). The resulting mixture was heated to reflux temperature and maintained at that temperature, with stirring, for 16 hours while removing water evolved from the reaction mixture. The resulting mixture was cooled, decanted and evaporated under high vacuum to afford the desired product as 117 g of a pale brown oil, TBN=0.87% N.

Example 4

(m=17 to 23, n=0, p=1, R=—NH—(CH$_2$CH$_2$NH)$_3$H)

To a 1000 ml flask, equipped with magnetic stirrer, Dean-Stark extractor and condenser, was added alkoxy acetic acid A (300 g, 0.18 mol), xylene (600 ml) and triethylenetetramine (23.6 g, 0.16 mol). The mixture was heated to reflux temperature and maintained at that temperature, with stirring, for 8 hours while removing water evolved from the reaction mixture. The resulting mixture was cooled to ambient temperature (20° C.), decanted and evaporated. The resulting product was dissolved in heptane (500 ml) and washed with sodium chloride (2×150 ml, saturated). The organic phase was then dried over MgSO$_4$, filtered and evaporated under high vacuum to afford the desired product as 315 g of a pale brown oil, TBN=0.75% N, AM=69.6%.

Example 5

(m=19, n=5, p=1, R=—NH CH$_2$CH$_2$N(CH$_2$CH$_2$NH$_2$)$_2$)

To a 500 ml flask, equipped with magnetic stirrer, Dean-Stark extractor and condenser, was added alkoxy acetic acid D (145 g, 0.09 mol), xylene (200 ml) and tris(2-aminoethyl) amine (10.2 g, 0.07 mol). The resulting mixture was heated to reflux temperature and maintained at that temperature, with stirring, for 8 hours while removing water evolved from the reaction mixture. The resulting mixture was cooled, filtered through "Celite" (trade mark) filter aid and evaporated. The resulting product was dissolved in heptane (500 ml), filtered through "Celite" filter aid and evaporated under high vacuum to afford the desired product as 147 g of a pale brown oil, TBN=0.61% N, AM=78.9%.

Example 6

(m=17 to 23, n=0, p=1, R=—$NHCH_2CH_2NHCH_2CH_2OH$)

To a 1000 ml flask, equipped with magnetic stirrer, Dean-Stark extractor and condenser, was added alkoxy acetic acid A (200 g, 0.12 mol), xylene (300 ml) and 2-(2-aminoethylamino)ethanol (12.6 g, 0.12 mol). The resulting mixture was heated to reflux temperature and maintained at that temperature, with stirring, for 6 hours while removing water evolved from the reaction mixture. The resulting mixture was cooled, decanted and evaporated under high vacuum to afford the desired product as 203 g of a pale brown oil, TBN=0.76% N, AM=88.5%.

Example 7

(m=17 to 23, n=0, p=1, R=—$NHCH_2CH_2NH_2$)

To a 1000 ml flask, equipped with magnetic stirrer, Dean-Stark extractor and condenser, was added alkoxy acetic acid A (200 g, 0.12 mol), xylene (300 ml) and ethylenediamine (70 g, 1.16 mol). The resulting mixture was heated to reflux temperature and maintained at that temperature, with stirring, for 8 hours while removing water evolved from the reaction mixture. The resulting mixture was cooled and evaporated under high vacuum to afford the desired product as 204 g of a pale brown oil, TBN=0.7% N, AM=86.6%.

Example 8

(m=17 to 23, n=0, p=1, R=—$OCH_2C(CH_2OH)_3$)

To a 5000 ml flask, equipped with mechanical stirrer, Dean-Stark extractor and condenser, was added pentaerythritol (51 g, 0.37 mol), dimethylsulphoxide (300 ml), xylene (200 ml) and para-toluene sulphonic acid (2 g). The resulting mixture was heated, with stirring, to 140° C. A solution of alkoxy acetic acid A (300 g, 0.2 mol) in xylene (100 ml) was added gradually over 2 hours. The temperature was maintained at 140° C., with stirring for 5 hours while removing water evolved from the reaction mixture. The resulting mixture was cooled, filtered and evaporated. The resulting residue was dissolved in hexane (500 ml) and washed with aqueous sodium chloride solution (3×250 ml). The organic phase was dried over $MgSO_4$, filtered and evaporated to afford the desired product as 328 g of a pale yellow oil.

Example 9

(m=120, n=0, p=1, R=—NH—$(CH_2CH_2NH)_2H$)

To a 1000 ml flask, equipped with magnetic stirrer, Dean-Stark extractor and condenser, was added alkoxy acetic acid C (200 g, 0.04 mol), xylene (200 ml) and diethylenetriamine (5.16 g, 0.05 mol). The resulting mixture was heated to reflux temperature and maintained at that temperature, with stirring, for 16 hours while removing water evolved from the reaction mixture. The resulting mixture was cooled and evaporated under high vacuum to afford the desired product as 204 g of a pale brown oil, TBN=0.34% N.

Example 10

(m=17 to 23, n=0, p=1, R=—$NHCH_2CH_2N(CH_2CH_2NHCO(CH_2)_2CH(CH_3)OH)_2$)

To a 250 ml flask, equipped with magnetic stirrer, was added a portion of the product of Example 1 (70 g, 0.04 mol) and gammavalerolactone (8 g, 0.08 mol). The resulting mixture was heated, with stirring at 145°–155° C. for 5 hours. The resulting mixture was evaporated under high vacuum to afford the desired product as a pale brown oil, 76 g, TBN=0.94.

Example 11

(m=17 to 23, n=0, p=1, R=—$NHCH_2CH_2N(CH_2CH_2NHCOCH_2N(CH_3)CH_2CH_2OH)_2$)

To a 250 ml flask, equipped with magnetic stirrer, was added a portion of the product of Example 1 (70 g, 0.04 mol) and N-methylmorpholinone (9.2 g, 0.08 mol). The resulting mixture was heated, with stirring at 145°–155° C. for 4 hours. The resulting mixture was evaporated under high vacuum to afford the desired product as a pale brown oil, 78 g, TBN=1.77% N, AM=89%.

Example 12

(m=3.5 to 5.5, n=0, p=1, R=—NH$(CH_2CH_2NH)_2H$)

To a 500 ml flask, equipped with magnetic stirrer, Dean-Stark extractor and condenser, was added alkoxy acetic acid B (100 g, 0.16 mol), xylene (150 ml) and diethylenetriamine (17.8 g, 0.17 mol). The resulting mixture was heated to reflux temperature and maintained at that temperature, with stirring, for 16 hours while removing water evolved from the reaction mixture. The resulting mixture was evaporated under high vacuum to afford the desired product as 106g of a pale brown oil, TBN=2.2% N, AM=92.3%.

Example 13

(m=17 to 23, n=0, p=2, R=—NH—$(CH_2CH_2NH)_4$—)

To a one litre flask, equipped with mechanical stirrer, Dean-Stark extractor and condenser, was added alkoxy acetic acid A (100 g, 0.06 mol), xylene (150 ml) and tetraethylenepentamine (5.3 g, 0.03 mol). The resulting mixture was heated to reflux temperature and maintained at that temperature, with stirring, for 16 hours while removing water evolved from the reaction mixture. The resulting mixture was evaporated under high vacuum to afford the desired product as 103g of a pale brown oil, TBN=0.86% N, AM=65%.

Example 14

(m=17 to 23, n=0, p=1, R=—NH—$(CH_2CH_2NH)_4H$)

To a one litre flask, equipped with mechanical stirrer, Dean-Stark extractor and condenser, was added alkoxy acetic acid A (200 g, 0.12 mol), xylene (150 ml) and tetraethylenepentamine (20.4 g, 0.11 mol). The resulting mixture was heated to reflux temperature and maintained at that temperature, with stirring, for 16 hours while removing water evolved from the reaction mixture. The resulting mixture was evaporated under high vacuum to afford the desired product as 197 g of a pale brown oil, TBN=2.1% N, AM=78%.

Example 15

(m=19, n=4, p=1, R=—$NHCH_2CH_2N(CH_2CH_2NH_2)_2$)

To a one litre flask, equipped with mechanical stirrer, Dean-Stark extractor and condenser, was added alkoxy acetic acid E (120 g, 0.08 mol), xylene (150 ml) and tris(2-aminoethyl)amine (7.8 g, 0.06 mol). The resulting mixture was heated to reflux temperature and maintained at that temperature, with stirring, for 16 hours while removing water evolved from the reaction mixture. The resulting mixture was evaporated under high vacuum to afford the desired product as 103 g of a pale yellow oil, TBN=0.99% N, AM=60%.

Example 16
(m=17 to 23, n=0, p=1, R=—NH(CH$_2$)$_4$NH$_2$)

To a one litre flask, equipped with mechanical stirrer, Dean-Stark extractor and condenser, was added alkoxy acetic acid A (150 g, 0.09 mol), toluene (200 ml) and 1,4-diaminobutane (16 g, 0.18 mol). The resulting mixture was heated to reflux temperature and maintained at that temperature, with stirring, for 16 hours while removing water evolved from the reaction mixture. The resulting mixture was evaporated, dissolved in chloroform (200 ml), washed with saturated aqueous sodium chloride solution (2×100 ml) and water (100 ml). The organic phase was dried over MgSO$_4$, filtered and evaporated under high vacuum to afford the desired product as 142 g of a pale yellow oil, TBN=0.54% N, AM=88%.

Example 17
(m=17 to 23, n=0, p=1, R=—NH(CH$_2$)$_3$NH$_2$)

To a one litre flask, equipped with mechanical stirrer, Dean-Stark extractor and condenser, was added alkoxy acetic acid A (150 g, 0.09 mol), toluene (200 ml) and 1,4-diaminopropane (13.5 g, 0.18 mol). The resulting mixture was heated to reflux temperature and maintained at that temperature, with stirring, for 16 hours while removing water evolved from the reaction mixture. The resulting mixture was evaporated, dissolved in chloroform (200 ml), washed with saturated aqueous sodium chloride solution (2×100 ml) and water (100 ml). The organic phase was dried over MgSO$_4$, filtered and evaporated under high vacuum to afford the desired product as 148 g of a pale yellow oil, TBN=0.58% N, AM=87%.

Example 18
(m=17 to 23, n=0, p=1, R=—NH—(CH$_2$CH$_2$O)$_2$—CH$_2$CH$_2$NH$_2$)

To a one litre flask, equipped with mechanical stirrer, Dean-Stark extractor and condenser, was added alkoxy acetic acid A (150 g, 0.09 mol), toluene (200 ml) and 2,2'-ethylenedioxybis(ethylamine) (26.9 g, 0.18 mol). The resulting mixture was heated to reflux temperature and maintained at that temperature, with stirring, for 16 hours while removing water evolved from the reaction mixture. The resulting mixture was evaporated, dissolved in chloroform (200 ml), washed with saturated aqueous sodium chloride solution (2×100 ml) and water (100 ml). The organic phase was dried over MgSO$_4$, filtered and evaporated under high vacuum to afford the desired product as 137 g of a pale yellow oil, TBN=0.58% N, AM=88%.

Example 19
(m=17 to 23, n=0, p=1, R=—NH(CH$_2$)$_3$(1,4-piperazinediyl)(CH$_2$)$_3$NH$_2$)

To a one litre flask, equipped with mechanical stirrer, Dean-Stark extractor and condenser, was added alkoxy acetic acid A (150 g, 0.09 mol), toluene (200 ml) and 1,4-bis(3-aminopropyl)piperazine (36.3 g, 0.18 mol). The resulting mixture was heated to reflux temperature and maintained at that temperature, with stirring, for 16 hours while removing water evolved from the reaction mixture. The resulting mixture was evaporated, dissolved in chloroform (200 ml), washed with saturated aqueous sodium chloride solution (2×100 ml) and water (100 ml). The organic phase was dried over MgSO$_4$, filtered and evaporated under high vacuum to afford the desired product as 151 g of a pale yellow oil, TBN=1.85% N, AM=88%.

Example 20
(m=17 to 23, n=0, p=1, R=—NH—(CH$_2$—CH$_2$—O)$_2$H)

To a one litre flask, equipped with mechanical stirrer, Dean-Stark extractor and condenser, was added alkoxy acetic acid A (30 g, 0.02 mol), toluene (50 ml) and 2-(2-aminoethoxy)ethanol (3.8 g, 0.04 mol). The resulting mixture was heated to reflux temperature and maintained at that temperature, with stirring, for 16 hours while removing water evolved from the reaction mixture. The resulting mixture was evaporated, dissolved in chloroform (100 ml), washed with saturated aqueous sodium chloride solution (2×50 ml) and water (50 ml). The organic phase was dried over MgSO$_4$, filtered and evaporated under high vacuum to afford the desired product as 32 g of a pale yellow oil, AM=87%.

Example 21
(m=17 to 23, n=0, p=1, R=—NH(CH$_2$)$_3$NH(CH$_2$)$_2$NH(CH$_2$)$_3$NH$_2$)

To a one litre flask, equipped with mechanical stirrer, Dean-Stark extractor and condenser, was added alkoxy acetic acid A (30 g, 0.02 mol), toluene (50 ml) and N,N'-bis(3-aminopropyl)ethylenediamine (6.3 g, 0.04 mol). The resulting mixture was heated to reflux temperature and maintained at that temperature, with stirring, for 16 hours while removing water evolved from the reaction mixture. The resulting mixture was evaporated, dissolved in chloroform (100 ml), washed with saturated aqueous sodium chloride solution (2×50 ml) and water (50 ml). The organic phase was dried over MgSO$_4$, filtered and evaporated under high vacuum to afford the desired product as 29 g of a pale yellow oil, TBN=1.17% N, AM=87%.

Example 22
(m=17 to 23, n=0, p=1, R=—NH—(CH$_2$CH$_2$CH$_2$NH)$_2$H)

To a one litre flask, equipped with mechanical stirrer, Dean-Stark extractor and condenser, was added alkoxy acetic acid A (30 g, 0.02 mol), toluene (50 ml) and N-(3-aminopropyl)-1,3-propanediamine (4.8 g, 0.04 mol). The resulting mixture was heated to reflux temperature and maintained at that temperature, with stirring, for 16 hours while removing water evolved from the reaction mixture. The resulting mixture was evaporated, dissolved in chloroform (100 ml), washed with saturated aqueous sodium chloride solution (2×50 ml) and water (50 ml). The organic phase was dried over MgSO$_4$, filtered and evaporated under high vacuum to afford the desired product as 33 g of a pale yellow oil, TEN=0.93% N, AM=88%.

Example 23
(m=17 to 23, n=0, p=1, R=—NH—(CH$_2$)$_3$—CH(CH$_2$NH$_2$)(CH$_3$)$_4$NH$_2$)

To a one litre flask, equipped with mechanical stirrer, Dean-Stark extractor and condenser, was added alkoxy acetic acid A (150 g, 0.09 mol), toluene (200 ml) and 4-(aminomethyl)-1,8-octanediamine (30.7 g, 0.18 mol). The resulting mixture was heated to reflux temperature and maintained at that temperature, with stirring, for 16 hours while removing water evolved from the reaction mixture. The resulting mixture was evaporated, dissolved in chloroform (200 ml), washed with saturated aqueous sodium chloride solution (2×100 ml) and water (100 ml). The organic phase was dried over MgSO$_4$, filtered and evaporated under high vacuum to afford the desired product as 159 g of a pale yellow oil, TEN=1.1% N, AM=87%.

Example 24
(m=17 to 23, n=0, p=2, R=—NH CH$_2$CH$_2$ N(CH$_2$CH$_2$NH$_2$) CH$_2$CH$_2$NH—)

To a one litre flask, equipped with mechanical stirrer, Dean-Stark extractor and condenser, was added alkoxy acetic acid A (150 g, 0.09 mol), toluene (150 ml) and tris(2-aminoethyl)amine (6.6 g, 0.04 mol). The resulting mixture was heated to reflux temperature and maintained at that temperature, with stirring, for 16 hours while removing water evolved from the reaction mixture. The resulting mixture was diluted with toluene (150 ml) and washed with sodium chloride solution (1×500 ml, saturated). The organic phase was dried over MgSO$_4$, filtered and evaporated under high vacuum to afford the desired product as 149 g of a pale yellow oil, TBN=0.77% N, AM=85%.

Example 25
(m=17 to 23, n=0, p=1, RH=[CH$_2$N((CH$_2$)$_2$CONH(CH$_2$) NH$_2$)$_2$]$_2$ To a 250 ml flask, equipped with magnetic stirrer, Dean-Stark extractor and condenser, was added "Starburst" (PAMAM, generation 0) dendrimer ("Starburst" is a trade mark) (ex Aldrich Chemical Company) (29 g, 0.01 mol, 20% solution in methanol) and xylene (100 ml). The resulting mixture was heated to reflux temperature and maintained at that temperature, with stirring, for 3 hours while removing methanol evolved from the reaction mixture. The resulting mixture was cooled to 90°–100° C. and a solution of alkoxy acetic acid A (20 g, 0.01 mol) in xylene (50 ml) was added over 30 minutes. The resulting mixture was heated to reflux temperature and maintained at that temperature, with stirring, for 16 hours while removing water evolved from the reaction mixture. The resulting mixture was evaporated, dissolved in heptane (100 ml), filtered through "Celite" (trade mark) filter aid and evaporated under high vacuum to afford the desired product as 21 g of a brown oil, TBN=1.6% N, AM$_S$=63%.

Example 26
(m=17 to 23, n=0, p=1, R=—NH—((CH$_2$)$_2$NH)$_x$—((CH$_2$)$_2$N(COCHOHC(CH$_3$)$_2$CH$_2$OH))$_y$—H where x+y=4)

To a one liter autoclave equipped with mechanical stirrer, was added toluene (500 ml), a portion of the product of Example 14 (125 g, 0.07 mol) and pantolactone (55 g, 0.42 mol). The autoclave was sealed, flushed with nitrogen and heated, with stirring, at 150°–160° for 15 hours. The resulting mixture was evaporated, dissolved in heptane (750 ml), washed with saturated aqueous sodium chloride solution (2×200 ml), dried over MgSO$_4$, filtered and evaporated under high vacuum to afford the desired product as 118 g of a brown oil. TBN 0.68% N, AM=85.2%

Example 27
(m=19, n=5, p=1, R=—NH—(CH$_2$)$_2$NH$_2$)

To a 150 ml flask, equipped with magnetic stirrer, Dean-Stark extractor and condenser, was added alkoxy acetic acid D (30 g, 0.02 mol), toluene (40 ml) and ethylenediamine (1.95 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over MgSO$_4$, filtered and evaporated to afford the desired product as 32 g of a pale yellow oil. TBN=0.43% N

Example 28
(m=19, n=5, p=1, R=—NH—(CH$_2$)$_3$NH$_2$)

To a 150 ml flask, equipped with magnetic stirrer, Dean-Stark extractor and condenser, was added alkoxy acetic acid D (30 g, 0.02 mol), toluene (40 ml) and propylenediamine (2.4 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over MgSO$_4$, filtered and evaporated to afford the desired product as 28 g of a pale yellow oil. TBN=0.24% N

Example 29
(m=19, n=5, p=1, R=—NH—(CH$_2$)$_4$NH$_2$)

To a 150 ml flask, equipped with magnetic stirrer, Dean-Stark extractor and condenser, was added alkoxy acetic acid D (30 g, 0.02 mol), toluene (40 ml) and butylenediamine (2.9 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over MgSO$_4$, filtered and evaporated to afford the desired product as 30 g of a pale yellow oil. TBN=0.56% N

Example 30
(m=19, n=5, p=1, R=—NH—(CH$_2$)$_5$NH$_2$)

To a 150 ml flask, equipped with magnetic stirrer, Dean-Stark extractor and condenser, was added alkoxy acetic acid D (10 g, 0.006 mol), toluene (30 ml) and 1,5-pentanediamine (1.2 g, 0.01 mol). The resulting mixture was heated to reflux temperature and maintained at that temperature, with stirring, for 16 hours while removing water evolved from the reaction mixture. The resulting mixture was cooled and evaporated. The resulting residue was dissolved in chloroform (50 ml) and washed with saturated aqueous sodium chloride solution (3×150 ml). The organic phase was dried over MgSO$_4$, filtered and evaporated to afford the desired product as 9 g of a pale yellow oil. TBN=0.62% N

Example 31
(m=19, n=5, p=1, R=—NH—(CH$_2$)$_6$NH$_2$)

To a 100 ml flask, equipped with magnetic stirrer, Dean-Stark extractor and condenser, was added alkoxy acetic acid D (10 g, 0.006 mol), toluene (30 ml) and 1,6-hexanediamine (1.3 g, 0.01 mol). The resulting mixture was heated to reflux temperature and maintained at that temperature, with stirring, for 16 hours while removing water evolved from the reaction mixture. The resulting mixture was cooled and evaporated. The resulting residue was dissolved in chloroform (50 ml) and washed with saturated aqueous sodium chloride solution (3×150 ml). The organic phase was dried over MgSO$_4$, filtered and evaporated to afford the desired product as 10 g of a pale yellow oil. TBN=0.53% N

Example 32
(m=19, n=5, p=1, R=—NH—(CH$_2$CH$_2$NH)$_2$—H)

To a 150 ml flask, equipped with magnetic stirrer, Dean-Stark extractor and condenser, was added alkoxy acetic acid D (30 g, 0.02 mol), toluene (40 ml) and diethylenetriamine (3.3 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over $MgSO_4$, filtered and evaporated to afford the desired product as 28 g of a pale yellow oil. TBN=0.89% N Example 33
(m=19, n=5, p=1, R=—NH—$CH_2CH_2$NH—$CH_2CH_2$OH)

To a 150 ml flask, equipped with magnetic stirrer, Dean-Stark extractor and condenser, was added alkoxy acetic acid D (30 g, 0.02 mol), toluene (40 ml) and 2-(2-aminoethylamino)ethanol (3.4 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over $MgSO_4$, filtered and evaporated to afford the desired product as 27 g of a pale yellow oil. TBN=0.53% N Example 34
(m=19, n=5, p=1, R=—NH—$(CH_2CH_2NH)_3$—H)

To a 150 ml flask, equipped with magnetic stirrer, Dean-Stark extractor and condenser, was added alkoxy acetic acid D (30 g, 0.02 mol), toluene (40 ml) and triethylenetetramine (4.7 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over $MgSO_4$, filtered and evaporated to afford the desired product as 33 g of a pale yellow oil. TBN=1.15% N Example 35
(m=19, n=5, p=1, R=—NH—$(CH_2CH_2NH)_4$—H To a 150 ml flask, equipped with magnetic stirrer, Dean-Stark extractor and condenser, was added alkoxy acetic acid D (30 g, 0.02 mol), toluene (40 ml) and tetraethylenepentamine (6.1 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over $MgSO_4$, filtered and evaporated to afford the desired product as 30 g of a pale yellow oil. TBN=1.65% N Example 36
(m=19, n=5, p=1, R=—NH—$(CH_2CH_2O)_2$—$CH_2CH_2NH_2$)

To a 150 ml flask, equipped with magnetic stirrer, Dean-Stark extractor and condenser, was added alkoxy acetic acid D (30 g, 0.02 mol), toluene (40 ml) and 2,2'-(ethylenedioxy)-bis(ethylamine) (4.8 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over $MgSO_4$, filtered and evaporated to afford the desired product as 27 g of a pale yellow oil. TEN=0.42% N Example 37
(m=19, n=5, p=1, R=—NH—$(CH_2CH_2CH_2NH)_2$—H)

To a 150 ml flask, equipped with magnetic stirrer, Dean-Stark extractor and condenser, was added alkoxy acetic acid D (30 g, 0.02 mol), toluene (40 ml) and dipropylenetriamine (4.3 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over $MgSO_4$, filtered and evaporated to afford the desired product as 33 g of a pale yellow oil. TBN=0.64% N Example 38
(m=19, n=5, p=1, R=—NH—$(CH_2)_3$NH$(CH_2N)_2$NH$(CH_2)_3NH_2$)

To a 150 ml flask, equipped with magnetic stirrer, Dean-Stark extractor and condenser, was added alkoxy acetic acid D (30 g, 0.02 mol), toluene (40 ml) and N,N-bis(3-aminopropyl)ethylene diamine (5.6 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over $MgSO_4$, filtered and evaporated to afford the desired product as 32 g of a pale yellow oil. TBN=1.12% N Example 39
(m=19, n=5, p=1, R=—NH—$(CH_2)_3$(1,4-piperazinediyl)$(CH_2)_3NH_2$)

To a 150 ml flask, equipped with magnetic stirrer, Dean-Stark extractor and condenser, was added alkoxy acetic acid D (30 g, 0.02 mol), toluene (40 ml) and 1,4-bis(3-aminopropyl)-piperazine (6.5 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over $MgSO_4$, filtered and evaporated to afford the desired product as 30 g of a pale yellow oil. TEN=0.97% N Example 40
(m=19, n=5, p=1, R=—NH—(4-(4-aminocyclohexylmethyl)-cyclohexyl)

To a 150 ml flask, equipped with magnetic stirrer, Dean-Stark extractor and condenser, was added alkoxy acetic acid D (30 g, 0.02 mol), toluene (40 ml) and 4,4-diaminodicyclohexylmethane (6.8 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over MgSO$_4$, filtered and evaporated to afford the desired product as 34 g of a pale yellow oil. TEN=0.86% N

Example 41
(m=19, n=5, p=1, R=—NH—CH$_2$C(CH$_3$)$_2$CH$_2$NH$_2$)

To a 150 ml flask, equipped with magnetic stirrer, Dean-Stark extractor and condenser, was added alkoxy acetic acid D (30 g, 0.02 mol), toluene (40 ml) and 2,2-dimethylpropane-1,3-diamine (3.3 g, 0.03 mol). The resulting mixture was heated to reflux temperature and maintained at that temperature, with stirring, for 8 hours while removing water evolved from the reaction mixture. The resulting mixture was cooled and evaporated. The resulting residue was dissolved in chloroform (50 ml) and washed with saturated aqueous sodium chloride solution (2×25 ml) and water (25 ml). The organic phase was dried over MgSO$_4$, filtered and evaporated to afford the desired product as 31 g of a pale yellow oil. TBN=0.53% N

Example 42
(m=19, n=5, p=1, R=—NH—CH$_2$-1,3,3-trimethyl-5-aminocyclohexyl)

To a 150 ml flask, equipped with magnetic stirrer, Dean-Stark extractor and condenser, was added alkoxy acetic acid D (30 g, 0.02 mol), toluene (40 ml) and isophoronediamine (5.6 g, 0.03 mol). The resulting mixture was heated to reflux temperature and maintained at that temperature, with stirring, for 16 hours while removing water evolved from the reaction mixture. The resulting mixture was cooled and evaporated. The resulting residue was dissolved in chloroform (100 ml) and washed with saturated aqueous sodium chloride solution (2×150 ml). The organic phase was dried over MgSO$_4$, filtered and evaporated to afford the desired product as 27 g of a pale yellow oil. TEN=0.91% N

Example 43
(m=19, n=5, p=1, R=—NH—(CH$_2$)$_3$CH(CH$_2$NH$_2$)(CH$_2$)$_4$NH$_2$)

To a 100 ml flask, equipped with magnetic stirrer, Dean-Stark extractor and condenser, was added alkoxy acetic acid D (10 g, 0.006 mol), toluene (30 ml) and 4-aminomethyl-1,8-octanediamine (1.9 g, 0.01 mol). The resulting mixture was heated to reflux temperature and maintained at that temperature, with stirring, for 16 hours while removing water evolved from the reaction mixture. The resulting mixture was cooled and evaporated. The resulting residue was dissolved in chloroform (50 ml) and washed with saturated aqueous sodium chloride solution (3×100 ml). The organic phase was dried over MgSO$_4$, filtered and evaporated to afford the desired product as 8 g of a pale yellow oil. TEN=0.67% N

Example 44
(m=19, n=5, p=1, R=—NH—(CH$_2$)$_3$N(CH$_3$)$_2$)

To a 100 ml flask, equipped with magnetic stirrer, Dean-Stark extractor and condenser, was added alkoxy acetic acid D (10 g, 0.006 mol), toluene (30 ml) and N,N-dimethyl-1,3-diaminopropane (1.2 g, 0.01 mol). The resulting mixture was heated to reflux temperature and maintained at that temperature, with stirring, for 16 hours while removing water evolved from the reaction mixture. The resulting mixture was cooled and evaporated. The resulting residue was dissolved in chloroform (50 ml) and washed with saturated aqueous sodium chloride solution (3×100 ml). The organic phase was dried over MgSO$_4$, filtered and evaporated to afford the desired product as 8 g of a pale yellow oil. TEN=0.21% N

Example 45
(m=19, n=5, p=1, R=—(O—CH$_2$C(CH$_2$OH)$_2$CH$_2$)$_2$—OH)

To a 100 ml flask, equipped with magnetic stirrer, Dean-Stark extractor and condenser, was added dipentaerythritol (3 g, 0.01 mol), dimethylsulphoxide (20 ml), xylene (30 ml) and para-toluene sulphonic acid (0.5 g). The resulting mixture was heated, with stirring, to 140° C. A solution of alkoxy acetic acid D (10 g, 0.006 mol) in xylene (20 ml) was added dropwise over 20 minutes. The temperature was maintained at 140° C., with stirring, for 15 hours, while removing water evolved from the reaction mixture. The resulting mixture was cooled and evaporated. The resulting residue was dissolved in hexane (50 ml) and washed with saturated aqueous sodium chloride solution (3×25 ml). The organic phase was dried over MgSO$_4$, filtered and evaporated to afford the desired product as 7 g of a pale yellow oil.

Example 46
(m=19, n=5, p=1, R=—(O—CH$_2$C(CH$_2$OH)$_2$CH$_2$)$_3$—OH)

To a 100 ml flask, equipped with magnetic stirrer, Dean-Stark extractor and condenser, was added tripentaerythritol (4.3 g, 0.01 mol), dimethylsulphoxide (20 ml), xylene (30 ml) and para-toluene sulphonic acid (0.5 g). The resulting mixture was heated, with stirring, to 1400C. A solution of alkoxy acetic acid D (10 g, 0.006 mol) in xylene (20 ml) was added dropwise over 20 minutes. The temperature was maintained at 140° C., with stirring, for 15 hours, while removing water evolved from the reaction mixture. The resulting mixture was cooled and evaporated. The resulting residue was dissolved in hexane (50 ml) and washed with saturated aqueous sodium chloride solution (3×25 ml). The organic phase was dried over MgSO$_4$, filtered and evaporated to afford the desired product as 12 g of a pale yellow oil.

Example 47
(m=19, n=5, p=5, R (H)$_p$=HO(CH$_2$C(CH$_2$OH)$_2$CH$_2$—O)$_3$H)

To a 100 ml flask, equipped with magnetic stirrer, Dean-Stark extractor and condenser, was added tripentaerythritol (0.4 g, 0.01 mol), dimethylsulphoxide (20 ml), xylene (40 ml) and para-toluene sulphonic acid (0.5 g). The resulting mixture was heated, with stirring, to 140° C. A solution of alkoxy acetic acid D (8.5 g, 0.005 mol) in xylene (20 ml) was added dropwise over 20 minutes. The temperature was maintained at 140° C., with stirring, for 15 hours, while removing water evolved from the reaction mixture. The resulting mixture was cooled and evaporated. The resulting residue was dissolved in hexane (150 ml) and washed with saturated aqueous sodium chloride solution (3×50 ml). The organic phase was dried over MgSO$_4$, filtered and evaporated to afford the desired product as 7 g of a pale yellow oil.

Example 48
(m=19, n=4, p=1, R=—NH—(CH$_2$CH$_2$NH)$_3$—H)

To a 500 ml flask, equipped with magnetic stirrer, air sparge with 200 micron frit, Dean-Stark collector and condenser, was added alkoxy acetic acid E (200 g, 0.12 mol) and triethylenetriamine (15 g, 0.1 mole). The resulting mixture was heated to 90°–110° C., with an air sparge rate of 100–200 ml/min and maintained at that temperature, with stirring, for 5 hours while removing water evolved from the reaction mixture. The resulting residue was dissolved in chloroform (350 ml) and washed with saturated aqueous sodium chloride solution (3×150 ml). The organic phase was dried over MgSO$_4$, filtered and evaporated to afford the desired product as 186g of a brown oil. TBN=0.76% N Comparative Example A (m=0, n=7, p=1, R=—N(CH$_2$CH$_2$CH$_2$CH$_3$)$_2$) (corresponds closely to the N, N-dibutyl amide (1) of Examples 1 and 2 of FR-A-2407258)

As starting material there was employed "DOBANOL" ethoxylate 25-7 ("DOBANOL" is a registered trade mark), available from member companies of the Royal Dutch/Shell group, corresponding to the above formula (Q) wherein m is 0, n is 7 and $R^1$ represents a $C_{12-15}$ alkyl group, having $M_n$ 515 and a kinematic viscosity of 31 mm²/s at 40° C. according to ASTM D 445.

To a one litre flask, equipped with mechanical stirrer and nitrogen purge, was added sodium hydride (64 g , 1.6 mol, 60% dispersion in oil) and tetrahydrofuran (100 ml). To this agitated mixture a solution of "DOBANOL" ethoxylate 25-7 (384 g , 0.76 mol) in tetrahydrofuran (500 ml) was added gradually over 2 hours. The resulting mixture was then heated to reflux temperature for 1 hour, cooled to 40°–50° C. and a solution of chloroacetic acid (75.6 g , 0.8 mol) in tetrahydrofuran (100 ml) was added gradually over 2 hours. The mixture was stirred at 20°–30° C. for 14 hours, heated at reflux temperature for 1 hour, cooled and then acidified with hydrochloric acid (2N aqueous solution). The resulting mixture was extracted with ether (3×500 ml) and the combined organic phase washed with saturated aqueous sodium chloride solution (2×200 ml). The organic phase was dried over $MgSO_4$, filtered and evaporated to afford the desired intermediate acid corresponding to formula R wherein m is 0 and n is 7, as 406 g of a pale yellow oil. AV=1.6 meqg$^{-1}$, AM=78%.

To a one litre flask, equipped with magnetic stirrer and condenser, was added thionyl chloride (60 ml). To this the above intermediate acid (200 g , 0.04 mol) was added gradually over approximately 2 hours. The resulting mixture was heated to reflux for 1 hour and excess thionyl chloride was removed by distillation. The resulting acid chloride was dissolved in toluene (100 ml) and added dropwise to a solution of dibutylamine (103 g , 0.8 mol) in toluene (200 ml) at such a rate as to maintain the reaction temperature below 25° C. The mixture was stirred for 1 hour, filtered and evaporated to afford the desired product as 263 g of a pale brown oil.

The products of Examples 1 to 48 and Comparative Example A were subjected to at least one of the following tests in liquid fuels:

(i) Intake Valve Deposit Simulator Test—Inclined Hot Plate Rig (ii) Intake Valve and Combustion Chamber Deposits using 1.2L Opel Kadett Engine (iii) Intake Valve Deposits using 2.3 L Mercedes Benz M-102E Engine (iv) Injector Fouling using 1.9 L Fiat Regata Indirect Injection Diesel Engine (i) Intake Valve Deposit Simulator Test—Inclined Hot Plate Rig This simulator test corresponds closely to that described in SAE Paper 890215, Daneshgari et al., "The Influence of Temperature upon Gasoline Deposit Build-Up on the Intake Valves", Detroit, USA, 27 Feb. to 3 Mar. 1989. The test rig utilizes four inclined plates in parallel. The plates are strips of sandblasted aluminum 50 cm long and 2.5 cm wide, having a central groove along their lengths 3 mm wide and 1 mm deep, mounted in the rig at an angle of 3 degrees relative to the horizontal. The temperature at the top end of each plate is maintained at 400° C. and at the middle of each plate is maintained at 250° C.

Gasoline samples, containing test materials at a concentration of non-volatile matter of 100 parts per million by weight (ppmw) in base fuel, are prepared, and 100 ml portions of the gasoline samples are delivered at a rate of 0.6 ml/minute from glass syringes fitted with 20 g auge steel hypodermic Luer lock needles into the groove at the top end of each plate. Once delivery is complete, after about 2 hours and 40 minutes, the plates are allowed to cool to ambient temperature (20° C.) and are washed with n-heptane until the run-off liquid is clear, and are then left to dry before assessment of any deposit present.

Assessment is made using a "SEESCAN" (trade mark) Marker Image analyzer with 512*512 image memory coupled to a "SONY"/"SEESCAN" (trade marks) CCD camera equipped with NIKON (trade mark) f55 Macro lens. Lighting of the plate being assessed is by two 12v Tungsten lamps mounted at a linear distance of 22 cm from the point on the plate upon which the camera is focused and at angles of 33 degrees and 147 degrees relative to the plate.

A clear portion of the plate is moved under the camera and an image thereof captured. The section of the plate containing deposit is then moved beneath the camera and an image thereof is captured. The image analyser divides, pixel by corresponding pixel, the deposit image by the clean image and automatically measures the area and optical density of deposit at the pixels contained within overall measuring frame, and calculates an intergrated optical density for the image, the numerical value of which is recorded as a test rating.

Results of this test are given in Table 1 as follows:

TABLE 1

| Test material (Example No) | Rating |
|---|---|
| 1 | 86 |
| 2 | 93 |
| 3 | 135 |
| 4 | 90 |
| 5 | 71 |
| 6 | 58 |
| 7 | 84 |
| 8 | 114 |
| 9 | 174 |
| 10 | 94 |
| 11 | 140 |
| 12 | 187 |
| 13 | 171 |
| 14 | 55 |
| 15 | 69 |
| 16 | 63 |
| 17 | 211 |
| 18 | 46 |
| 19 | 75 |
| 20 | 214 |
| 21 | 114 |
| 22 | 61 |
| 23 | 75 |
| 24 | 79 |
| 25 | 124 |
| 26 | 71 |
| 27 | 30 |
| 28 | 162 |
| 29 | 53 |
| 30 | 49 |
| 31 | 46 |
| 32 | 25 |
| 33 | 32 |
| 34 | 23 |
| 35 | 47 |
| 36 | 42 |
| 37 | 78 |
| 38 | 77 |
| 39 | 49 |
| 40 | 171 |
| 41 | 190 |
| 42 | 41 |
| 43 | 106 |
| 44 | 84 |
| 45 | 151 |
| 46 | 169 |
| 47 | 109 |
| 48 | 187 |

TABLE 1-continued

| Test material (Example No) | Rating |
|---|---|
| Comp. A | 246 |
| Base Fuel | 266 |

In Table 1, the lower the rating the better. Accordingly, it can readily be seen that the results for all of the test materials of Examples 1 to 48 are superior both to that for Comparative Example A and for base gasoline.

(ii) Intake Valve and Combustion Chamber Deposits using 1.2L Opel Kadett Engine

The test materials of a number of the Examples have been tested in a laboratory multicylinder engine to evaluate their intake valve and combustion chamber deposit control performance. This engine was a 1.2 L twin carburetor four cylinder spark-ignition engine manufactured by General Motors' Opel subsidiary and is used in the published inlet system cleanliness test CEC F-04-A-87. Is has 79 mm bore, 61 mm stroke and is operated under a prescribed load and speed schedule representative of typical driving conditions as set forth in Table 2.

TABLE 2

| Step | Time, sec | Load, Nm | Speed, r/min |
|---|---|---|---|
| 1 | 30 | 0 | 1200 |
| 2 | 60 | 35 | 3000 |
| 3 | 60 | 29 | 1300 |
| 4 | 120 | 32 | 1850 |

In modifying the procedure, the air inlet was maintained at 25° C. (+ or −2 degrees) and no extra oil injection down the valve guides was used. The lubricating oil in the sump was "SHELL" "HELIX" 10 w/40 lubricating oil (API SG quality). The test duration was 40 hours including 2 hour shutdowns after the first and second 12 hour running periods. A twin carburetor set up was used to enable two additives to be tested simultaneously. Consequently, intake valve and combustion chamber deposit weights are average values from 2 cylinders.

All the tests were conducted on the same base gasoline representative of commercial unleaded fuel. This had a RON of 100.0 and a MON of 88.5, contained 57.1% v aromatics with 4.0% v olefins (ASTM D1319), and had a final boiling point of 211° C. (ASTM D86).

The test materials were all incorporated in the base gasoline together with a polyalphaolefin (PAO). The polyalphaolefin was a hydrogenated oligomer of decene-1 having a viscosity at 100° C. of $8 \times 10^{-6}$ m$^2$/s (8 centistokes). The concentration in the resulting gasoline compositions of the test materials was 500 ppmw (non-volatile matter), unless otherwise indicated, and of the polyalphaolefin was 500 ppmw.

Results of these tests are given in Table 3 following:

TABLE 3

| Test material (Example No.) | Deposits in Opel Kadett Engine | |
|---|---|---|
| | Intake valve deposit (mg/valve) | Combustion Chamber Deposit (mg/cylinder) |
| 1 | 2 | 1026 |
| 1 (no PAO) | 0 | 1217 |

TABLE 3-continued

| Test material (Example No.) | Deposits in Opel Kadett Engine | |
|---|---|---|
| | Intake valve deposit (mg/valve) | Combustion Chamber Deposit (mg/cylinder) |
| 1 (250 ppmw) | 17 | 1059 |
| 3 | 5 | 1265 |
| 4 | 6 | 1180 |
| 5 | 20 | 1051 |
| 6 | 36 | 1151 |
| 7 | 0 | 1238 |
| 8 | 68 | 1068 |
| 9 | 169 | 1326 |
| 10 | 3 | 1260 |
| 11 | 0 | 1034 |
| 12 | 9 | 1271 |
| 13 | 5 | 1167 |
| 14 | 13 | 1255 |
| 24 | 17 | 1100 |
| Comp. A | 51 | 1441 |
| Base gasoline + 500 ppm PAO | 179 | 1171 |
| Base gasoline alone | 280 | 1179 |

In tests on additional compounds a different base gasoline was used. This had a RON of 98.7 and a MON of 87.3, contained 48% v aromatics with 7.5% v olefins, (ASTM D1319) and had a final boiling point of 208° C. (ASTM D86).

Results of these tests are given in Table 3a following.

TABLE 3a

| Test material (Example No.) | Deposits in Opel Kadett Engine | |
|---|---|---|
| | Intake valve deposit (mg/valve) | Combustion Chamber Deposit (mg/cylinder) |
| 5 | 1 | 976 |
| 15 | 4 | 1269 |
| 16 | 4 | 1097 |
| 17 | 20 | 1121 |
| 18 | 2 | 1173 |
| 19 | 23 | 1011 |
| 23 | 24 | 1298 |
| 26 | 4 | 1126 |
| 34 | 0 | 930 |
| Base gasoline + 500 ppm PAO | 177 | 1112 |
| Base gasoline alone | 267 | 937 |

It will be noted that all of the gasoline compositions containing test materials of the present invention gave lower combustion chamber deposits than that containing the material of Comparative Example A, that all of the gasoline compositions containing test materials of the present invention also gave lower intake valve deposits than either the base gasoline or the base gasoline plus PAO, and that all but two of the gasoline compositions containing test materials of the present invention also gave lower intake valve deposits than that containing the material of Comparative Example A.

A modification of the above procedure was used to investigate the clean-up potential of the test materials of the present invention. In a first phase a clean engine is run on base gasoline for 20 hours under the schedule of Table 2, with CEC RL-51 reference lubricating oil in the engine sump. The engine is then dismantled and the weight of intake valve deposit measured. In the second phase the intake valves are replaced in their original orientation, without being cleaned, a new oil filter is fitted to the engine and the lubricating oil in the sump is changed to "SHELL" "HELIX" 10 w/40 lubricating oil (API SG quality) ("SHELL" and "HELIX" are registered trade marks). The engine is run using test fuel as above for 60 hours under the schedule of Table 2, and the weight of intake valve deposit is then measured and compared with that at the end of the first phase.

The clean-up test procedure was followed using (1) a gasoline composition containing 500 ppmw non-volatile matter of the test material of Example 1 and, for comparison purposes, (2) using base gasoline.

At the end of the second phase, the intake valve deposits were found to be reduced by 48% in the case of the gasoline composition containing the test material of Example 1, whereas the intake valve deposits had increased by 35% in the case of the base gasoline.

(iii) Intake Valve Deposits using 2.3 L Mercedes Benz Engine

The test material of Example 1 and that of Comparative Example A have also been tested in relation to intake valve deposits in a 2.3 L Mercedes Benz 102E four cylinder spark-ignition engine according to the published test procedure CEC-F-05-A95.

The tests were effected using different base gasolines (Fuels I and II) due to availability reasons at the times when the tests were made. Fuel I had a RON of 98.6 and a MON of 86.2, contained 46% v aromatics with 9.4% v olefins (ASTM D 1319) and had initial boiling point of 29° C., 50% boiling temperature of 113° C. and final boiling point of 203° C. (ASTM D 86). Fuel II had a RON of 98.7 and a MON of 87.6, contained 52% v aromatics with 9.4% v olefins (ASTM D 1319) and had initial boiling point of 28°0 C., 50% boiling temperature of 121° C. and final boiling point of 208° C. (ASTM D86).

In some of the compositions, PAO and Polyether A were employed as carrier fluids. Quantities of the test materials are expressed in ppmw of non-volatile matter. Fuel compositions and test data are given in Table 4 following, wherein the rating is in accordance with CEC-F-05-A95, wherein 10 represents completely clean, and 0 completely blackened (i.e. the larger the value of the rating, the better).

TABLE 4

| Test Material (Example No.) | 2.3L Mercedes Benz Engine | |
|---|---|---|
| | Intake Valve Deposits (mg/valve) | Rating |
| Base Fuel I | 452 | 7.3 |
| Base Fuel plus 1 (200 ppmw) | 5 | 9.8 |
| 1 (132 ppmw, + 200 ppmw PAO + 200 ppmw Polyether A) | 0 | 9.8 |
| Base Fuel II | 359 | 7.5 |
| Base Fuel II plus Comp. A (132 ppmw, + 200 ppmw PAO + 200 ppmw Polyether A) | 93 | 8.8 |

It will be observed in Table 4 that not only are the various values in relation to gasoline compositions containing test material of Example 1 significantly superior to that containing test material of Comparative Example A, but these were achieved in a base gasoline (Base Fuel I) which had a greater tendency to foul the inlet valves than the base gasoline (Base Fuel II) used for comparison purposes.

(iv) Injector Fouling using 1.9 L Fiat Regata Indirect Injection Diesel Engine

Diesel engine tests were performed using the test material of Example 1 dissolved at a concentration of 400 ppmw (non-volatile matter) in a base diesel fuel which was a blended diesel oil (without additives) in accordance with BS 2869, having cetane value in the range 50 to 53, and, for comparison purposes, with this same base diesel fuel per se.

These tests were performed according to the following method, employing a Fiat IDI (indirect injection) 1929 cc, type 149 Al.000, diesel engine as used in Fiat Regata diesel automobiles.

The engine was warmed up at 1500 rpm engine speed and 25Nm dynamometer load for 20 mins. Injector nozzles were then changed to test nozzles.

The engine was then run at 2700 rpm and 75 Nm for 8.5 hours, after which the engine was switched off. Coolant oil/water temperatures were maintained at 90°±4° C.

Performance of each diesel fuel was assessed qualitatively by air-flow measurement of fouling levels produced in the engine's injector nozzles. The nozzles, of type Bosch DN 12 SD 1750, were placed in a Ricardo air-flow rig according to ISO 4010, and air-flow measurements were recorded at needle lifts of 0.1, 0.2 and 0.3 mm, with a vacuum pressure 600 m Bar (60,000 Pa).

Build up of deposits in the nozzles causes a reduction in measured air-flow, and degree of nozzle fouling can be quantified by the formula:

$$\text{Nozzle Fouling} = \frac{\text{Flow (clean)} - \text{Flow (fouled)}}{\text{Flow (Clean)}} \times 100$$

where "clean" values were measured prior to engine test and "fouled" values were measured after engine test.

Average fouling level (averages of values at the three needle lift levels) were as follows:

| Fuel (Example) | Fouling level (%) |
|---|---|
| 1 | 2 |
| Base Fuel | 55 to 65 |

It can thus be seen that very much reduced fouling level resulted when the test material of Example 1 was employed.

In addition to the effects evidenced by the above tests, observations have suggested that products of formula I, in accordance with the invention, may promote flaking and removal of combustion chamber deposits in spark-ignition engines by spontaneous deadhesion of such deposits. At certain concentrations in fuels, products of formula I may confer a level of anti-rust protection.

What is claimed is:

1. An alkoxy acetic acid derivative of general formula I:

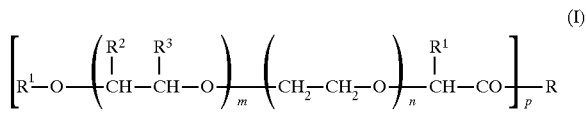

(I)

wherein R is the residue of an amine, an aminoalcohol or a polyol linked to the or each —CHR'—CO— moiety via an amide or ester linkage:

R' is hydrogen or $C_{1-4}$ alkyl;

$R^1$ is an optionally substituted hydrocarbyl group of 1 to 300 carbon atoms;

one of $R^2$ and $R^3$ is independently selected from hydrogen and optionally substituted hydrocarbyl of 1 to 10 carbon atoms, the other of $R^2$ and $R^3$ being independently selected from optionally substituted hydrocarbyl of 1 to 10 carbon atoms;

m is from 3 to 200;

n is from 0 to 20, provided that m/n is at least 1; and
p is from 1 to 5.

2. The acid derivative of claim 1 wherein R' is hydrogen.

3. The acid derivative of claim 1 wherein p is 1 or 2.

4. The acid derivative of claim 1 wherein m is from 3 to 150 and n is from 0 to 10.

5. The acid derivative of claim 1 wherein one of $R^2$ and $R^3$ is hydrogen, the other being a $C_{1-3}$ alkyl group.

6. The acid derivative of claim 1 wherein $R^1$ represents a $C_{1-20}$ alkyl group, a phenyl or benzyl group or a ($C_{1-15}$ alkyl) phenyl or ($C_{1-18}$ alkyl) benzyl group.

7. The acid derivative of claim 6 wherein $R^1$ represents a $C_{10-15}$ alkyl group.

8. The acid derivative of claim 1, which is derived from the compound of R(H)p, of which R represents the residue, has the general formula II:

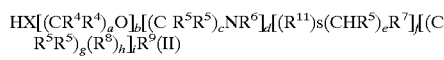

wherein X is O or $NR^6$, each $R^4$ independently represents hydrogen, hydrocarbyl of 1 to 10 carbon atoms or hydrocarbyl of 1 to 10 carbon atoms substituted by at least one hydroxy group, each $R^5$ independently represents hydrogen or hydrocarbyl of 1 to 10 carbon atoms, each $R^6$ independently represents hydrogen or hydrocarbyl of 1 to 10 carbon atoms, $R^7$ represents a $C_{5-7}$ cycloalkanediyl—NH— or 1,4-piperazinediyl moiety optionally substituted by one or more hydrocarbyl groups of 1 to 10 carbon atoms, each $R^8$ independently represents $NR^{10}$ or $CHR^{10}$, $R^9$ represents hydrogen, hydrocarbyl of 1 to 30 carbon atoms or a —CO(CHOH)$_d$(CHR$^5$)$_f$(NR$^5$)$_k$(CHR$^5$)$_l$OH group, $R^{10}$ represents a —(CR$^5$R$^5$)$_r$NR$^6$R$^9$ group, $R^{11}$ represents a $C_{5-7}$ cycloalkanediyl moiety optionally substituted by one or more hydrocarbyl groups of 1 to 10 carbon atoms, a is 1 to 10,
b is 0 to 10,
c is 1 to 10,
d is 0 to 10,
e is 1 to 10,
f is 0 or 1,
g is 1 to 10,
h is 0 or 1
i is 0 to 10
j is 1 to 10,
k is 0 or 1,
l is 1 to 10,
r is 1 to 10,
s is 0 or 1, and
t is 0 or 1, and integers b, d, f and i indicate numbers of associated moieties present, and the various moieties [(CR$^4$R$^4$)$_a$O], [(C R$^5$R$^5$)$_c$NR$^6$], [(CHR$^5$)$_e$R$^7$] and [(C R$^5$R$^5$)$_g$(R$^8$)$_h$] may be in any linear order.

9. The acid derivative of claim 8 wherein in formula II X is O or $NR^6$, each $R^4$ independently represents hydrogen, $C_{1-4}$ alkyl or $C_{1-4}$ hydroxyalkyl, each $R^5$ independently represents hydrogen or $C_{1-4}$ alkyl, each $R^6$ represents hydrogen or methyl, $R^7$ represents a 1,4-piperazinediyl moiety or a cyclohexanediyl-NH— moiety optionally substituted by up to three methyl groups, each $R^8$ independently represents $NR^{10}$ or $CHR^{10}$, $R^9$ represents hydrogen or a —CO(CHOH)$_a$(CHR$^5$)$_b$(NR$^5$)$_k$(CHR$^5$)$_l$OH group, $R^{10}$ represents a —(CHR$^5$)$_r$NHR$^9$ group, $R^{11}$ represents a cyclohexanediyl moeity optionally substituted by up to three methyl groups, a is 1 to 6, b is 0 to 5, c is 1 to 6, d is 0 to 5, e is 1 to 5, f is 0 or 1, g is 1 to 5, h is 0 or 1, i is 0 to 5, j is 1 to 5, k is 0 or 1, l is 1 to 5, r is 1 to 5, s is 0 or 1 and t is 0 or 1.

10. The acid derivative of claim 9 wherein R(H)$_p$ is selected from the group consisting of pentaerythritol, triethylenetetramine and tris(2-aminoethyl)amine.

11. A process for preparing an acid derivative of formula I as defined in claim 1 which comprises reacting a compound of general formula III:

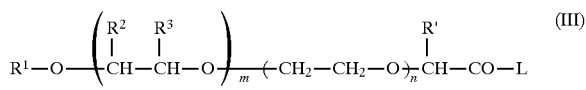

wherein R', $R^1$, $R^2$, $R^3$, m and n are as defined in claim 1 and L represents a leaving group, with a compound of general formula R(H)$_p$, wherein R is as defined in claim 1 in molar ratio compound of formula III: compound of formula R(H)$_p$ of substantially p:1, optionally followed by converting the resulting acid derivative of formula I into another acid derivative of formula I with different group R as defined in claim 1.

12. An additive concentrate suitable for addition to fuel for an internal combustion engine which comprises a fuel-compatible diluent and an acid derivative of formula I as defined in claim 1.

13. A fuel composition comprising a major amount of a fuel for an internal combustion engine and a minor amount of an acid derivative of formula I as defined in claim 1.

14. A method of operating an internal combustion engine which comprises introducing into the combustion chambers of said engine a fuel composition according to claim 13.

15. The additive concentrate of claim 12 wherein R' is hydrogen.

16. The additive concentrate of claim 12 wherein p is 1 or 2.

17. The additive concentrate of claim 12 wherein m is from 3 to 150 and n is from 0 to 10.

18. The additive concentrate of claim 12 wherein one of $R^2$ and $R^3$ is hydrogen, the other being a $C_{1-3}$ alkyl group.

19. The additive concentrate of claim 12 wherein $R^1$ represents a $C_{1-20}$ alkyl group, a phenyl or benzyl group or a ($C_{1-15}$ alkyl) phenyl or ($C_{1-15}$ alkyl) benzyl group.

20. The additive concentrate of claim 12 wherein $R^1$ represents a $C_{10-18}$ alkyl group.

21. The additive concentrate of claim 12, which is derived from the compound of R(H)p, of which R represents the residue, has the general formula II:

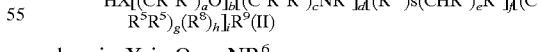

wherein X is O or $NR^6$, each $R^4$ independently represents hydrogen, hydrocarbyl of 1 to 10 carbon atoms or hydrocarbyl of 1 to 10 carbon atoms substituted by at least one hydroxy group, each $R^5$ independently represents hydrogen or hydrocarbyl of 1 to 10 carbon atoms, each $R^6$ independently represents hydrogen or hydrocarbyl of 1 to 10 carbon atoms, $R^7$ represents a $C_{5-7}$ cycloalkanediyl-NH— or 1,4-piperazinediyl moiety optionally substituted by one or more hydrocarbyl groups of 1 to 10 carbon atoms,

35 each R⁸ independently represents NR¹⁰ or CHR¹⁰,
R⁹ represents hydrogen, hydrocarbyl of 1 to 30 carbon atoms or a —CO(CHOH)$_f$(CHR⁵)$_j$(NR⁵)$_k$(CHR⁵)$_l$OH group,
R¹⁰ represents a —(CR⁵R⁵)$_r$NR⁶R⁹ group,
R¹¹ represents a C$_{5-7}$ cycloalkanediyl moiety optionally substituted by one or more hydrocarbyl groups of 1 to 10 carbon atoms,
a is 1 to 10,
b is 0 to 10,
c is 1 to 10,
d is 0 to 10,
e is 1 to 10,
f is 0 or 1,
g is 1 to 10,
h is 0 or 1
i is 0 to 10
j is 1 to 10,
k is 0 or 1,
i is 1 to 10,
r is 1 to 10,
s is 0 or 1, and
t is 0 or 1,
and integers b, d, f and i indicate numbers of associated moieties present, and the various moieties [(CR⁴R⁴)$_a$O], [(C R⁵R⁵)$_c$NR⁶], [(CHR⁵)$_e$R⁷] and [(C R⁵R⁵)$_g$(R⁸)$_h$] may be in any linear order.

22. The additive concentrate of claim 20 wherein in formula II X is 0 or NR⁶, each R⁴ independently represents hydrogen, C$_{1-4}$ alkyl or C$_{1-4}$ hydroxyalkyl, each R⁵ independently represents hydrogen or C$_{1-4}$ alkyl, each R⁶ represents hydrogen or methyl, R⁷ represents a 1,4-piperazinediyl moiety or a cyclohexanediyl-NH— moiety optionally substituted by up to three methyl groups, each R⁸ independently represents NR¹⁰ or CHR¹⁰, R⁹ represents hydrogen or a —CO(CHOH)$_f$(CHR⁵)$_j$(NR⁵)$_k$(CHR⁵)$_l$OH group, R¹⁰ represents a —(CHR⁵)$_r$NHR⁹ group, R¹¹ represents a cyclohexanediyl moiety optionally substituted by up to three methyl groups, a is 1 to 6, b is 0 to 5, c is 1 to 6, d is 0 to 5, e is 1 to 5, f is 0 or 1, g is 1 to 5, h is 0 or 1, i is 0 to 5, j is 1 to 5, k is 0 or 1, l is 1 to 5, r is 1 to 5, s is 0 or 1 and t is 0 or 1.

23. The additive concentrate of claim 22 wherein R(H)$_p$ is selected from the group consisting of pentaerythritol, triethylenetetramine and tris(2-aminoethyl)amine.

24. The fuel composition of claim 13 wherein R' is hydrogen.

25. The fuel composition of claim 13 wherein p is 1 or 2.

26. The fuel composition of claim 13 wherein m is from 3 to 150 and n is from 0 to 10.

27. The fuel composition of claim 13 wherein one of R² and R³ is hydrogen, the other being a C$_{1-3}$ alkyl group.

28. The fuel composition of claim 13 wherein R¹ represents a C$_{1-20}$ alkyl group, a phenyl or benzyl group or a (C$_{1-15}$ alkyl) phenyl or (C$_{1-15}$ alkyl) benzyl group.

29. The fuel composition of claim 28 wherein R¹ represents a C$_{10-18}$ alkyl group.

30. The fuel composition of claim 13, which is derived from the compound of R(H)p, of which R represents the residue, has the general formula II:

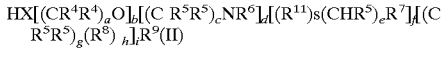
HX[(CR⁴R⁴)$_a$O]$_b$[(C R⁵R⁵)$_c$NR⁶]$_d$[(R¹¹)s(CHR⁵)$_e$R⁷]$_f$[(C R⁵R⁵)$_g$(R⁸)$_h$]$_i$R⁹(II)

wherein X is O or NR⁶,

36 each R⁴ independently represents hydrogen, hydrocarbyl of 1 to 10 carbon atoms or hydrocarbyl of 1 to 10 carbon atoms substituted by at least one hydroxy group,
each R⁵ independently represents hydrogen or hydrocarbyl of 1 to 10 carbon atoms,
each R⁶ independently represents hydrogen or hydrocarbyl of 1 to 10 carbon atoms,
R⁷ represents a C$_{5-7}$ cycloalkanediyl-NH— or 1,4-piperazinediyl moiety optionally substituted by one or more hydrocarbyl groups of 1 to 10 carbon atoms,
each R⁸ independently represents NR¹⁰ or CHR¹⁰,
R⁹ represents hydrogen, hydrocarbyl of 1 to 30 carbon atoms or a —CO(CHOH)$_f$(CHR⁵)$_j$(NR⁵)$_k$(CHR⁵)$_l$OH group,
R¹⁰ represents a —(CR⁵R⁵)$_{NR}$⁶R⁹ group,
R¹¹ represents a C$_{5-7}$ cycloalkanediyl moiety optionally substituted by one or more hydrocarbyl groups of 1 to 10 carbon atoms,
a is 1 to 10,
b is 0 to 10,
c is 1 to 10,
d is 0 to 10,
e is 1 to 10,
f is 0 or 1,
g is 1 to 10,
h is 0 or 1
i is 0 to 10
j is 1 to 10,
k is 0 or 1,
l is 1 to 10,
r is 1 to 10,
s is 0 or 1, and
t is 0 or 1,
and integers b, d, f and i indicate numbers of associated moieties present, and the various moieties [(CR⁴R⁴)$_a$O], [(C R⁵R⁵)$_c$NR⁶], [(CHR⁵)$_e$R⁷] and [(C R⁵R⁵)$_g$(R⁸)$_h$] may be in any linear order.

31. The fuel composition of claim 30 wherein in formula II X is 0 or NR⁶, each R⁴ independently represents hydrogen, C$_{1-4}$ alkyl or C$_{1-4}$ hydroxyalkyl, each R⁵ independently represents hydrogen or C$_{1-4}$ alkyl, each R⁶ represents hydrogen or methyl, R⁷ represents a 1,4-piperazinediyl moiety or a cyclohexanediyl-NH— moiety optionally substituted by up to three methyl groups, each R⁸ independently represents NR¹⁰ or CHR¹⁰, R⁹ represents hydrogen or a —CO(CHOH)$_f$(CHR⁵)$_j$(NR⁵)$_k$(CHR⁵)$_l$OH group, R¹⁰ represents a —(CHR⁵)$_r$NHR⁹ group, R¹¹ represents a cyclohexanediyl moiety optionally substituted by up to three methyl groups, a is 1 to 6, b is 0 to 5, c is 1 to 6, d is 0 to 5, e is 1 to 5, f is 0 or 1, g is 1 to 5, h is 0 or 1, i is 0 to 5, j is 1 to 5, k is 0 or 1, l is 1 to 5, r is 1 to 5, s is 0 or 1 and t is 0 or 1.

32. The fuel composition of claim 31 wherein R(H)$_p$ is selected from the group consisting of pentaerythritol, triethylenetetramine and tris(2-aminoethyl)amine.

33. The method of claim 14 wherein R' is hydrogen.

34. The method of claim 14 wherein p is 1 or 2.

35. The method of claim 14 wherein m is from 3 to 150 and n is from 0 to 10.

36. The method of claim 14 wherein one of R² and R³ is hydrogen, the other being a C$_{1-3}$ alkyl group.

37. The method of claim 14 wherein R¹ represents a C$_{1-20}$ alkyl group, a phenyl or benzyl group or a (C$_{1-15}$ alkyl) phenyl or (C$_{1-15}$ alkyl) benzyl group.

38. The method of claim 37 wherein $R^1$ represents a $C_{10-18}$ alkyl group.

39. The method of claim 14, which is derived from the compound of R(H)p, of which R represents the residue, has the general formula II:

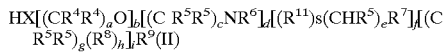

wherein X is O or $NR^6$, each $R^4$ independently represents hydrogen, hydrocarbyl of 1 to 10 carbon atoms or hydrocarbyl of 1 to 10 carbon atoms substituted by at least one hydroxy group, each $R^5$ independently represents hydrogen or hydrocarbyl of 1 to 10 carbon atoms, each $R^6$ independently represents hydrogen or hydrocarbyl of 1 to 10 carbon atoms, $R^7$ represents a $C_{5-7}$ cycloalkanediyl-NH— or 1,4-piperazinediyl moiety optionally substituted by one or more hydrocarbyl groups of 1 to 10 carbon atoms, each $R^8$ independently represents $NR^{10}$ or $CHR^{10}$, $R^9$ represents hydrogen, hydrocarbyl of 1 to 30 carbon atoms or a —CO(CHOH)$_i$(CHR$^5$)$_j$(NR$^5$)$_k$(CHR$^5$)$_l$OH group, $R^{10}$ represents a —(CR$^5$R$^5$)$_r$NR$^6$R$^9$ group, $R^{11}$ represents a $C_{5-7}$ cycloalkanediyl moiety optionally substituted by one or more hydrocarbyl groups of 1 to 10 carbon atoms, a is 1 to 10,
b is 0 to 10,
c is 1 to 10,
d is 0 to 10,
e is 1 to 10,
f is 0 or 1,
g is 1 to 10,
h is 0 or 1
i is 0 to 10
j is 1 to 10,
k is 0 or 1,
i is 1 to 10,
r is 1 to 10,
s is 0 or 1, and
t is 0 or 1, and integers b, d, f and i indicate numbers of associated moieties present, and the various moieties [(CR$^4$R$^4$)$_a$O], [(C R$^5$R$^5$)$_c$NR$^6$], [(CHR$^5$)$_e$R$^7$] and [(C R$^5$R$^5$)$_g$(R$^8$)$_h$] may be in any lines order.

40. The method of claim 39 wherein in formula II X is O or $NR^6$, each $R^4$ independently represents hydrogen, $C_{1-4}$ alkyl or $C_{1-4}$ hydroxyalkyl, each $R^5$ independently represents hydrogen or $C_{1-4}$ alkyl, each $R^6$ represents hydrogen or methyl, $R^7$ represents a 1,4-piperazinediyl moiety or a cyclohexanediyl-NH— moiety optionally substituted by up to three methyl groups, each $R^8$ independently represents $NR^{10}$ or $CHR^{10}$, $R^9$ represents hydrogen or a —CO(CHOH)$_i$(CHR$^5$)$_j$(NR$^5$)$_k$(CHR$^5$)$_l$OH group, $R^{10}$ represents a —(CHR$^5$)$_r$NHR$^9$ group, $R^{11}$ represents a cyclohexanediyl moiety optionally substituted by up to three methyl groups, a is 1 to 6, b is 0 to 5, c is 1 to 6, d is 0 to 5, e is 1 to 5, f is 0 or 1, g is 1 to 5, h is 0 or 1, i is 0 to 5, j is 1 to 5, k is 0 or 1, l is 1 to 5, r is 1 to 5, s is 0 or 1 and t is 0 or 1.

41. The method of claim 40 wherein R(H)$_p$ is selected from the group consisting of pentaerythritol, triethylenetetramine and tris(2-aminoethyl)amine.

* * * * *